(12) United States Patent
Yanagi et al.

(10) Patent No.: US 10,030,266 B2
(45) Date of Patent: Jul. 24, 2018

(54) SEMICONDUCTOR DEVICE AND MANUFACTURING METHOD THEREOF

(71) Applicant: HITACHI, LTD., Chiyoda-ku, Tokyo (JP)

(72) Inventors: Itaru Yanagi, Tokyo (JP); Riichiro Takemura, Tokyo (JP); Yoshimitsu Yanagawa, Tokyo (JP); Takahide Yokoi, Tokyo (JP); Takashi Anazawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/895,923

(22) PCT Filed: Jun. 27, 2013

(86) PCT No.: PCT/JP2013/067723
§ 371 (c)(1),
(2) Date: Dec. 3, 2015

(87) PCT Pub. No.: WO2014/207877
PCT Pub. Date: Dec. 31, 2014

(65) Prior Publication Data
US 2016/0122815 A1    May 5, 2016

(51) Int. Cl.
*C12Q 1/6874* (2018.01)
*H01L 29/49* (2006.01)
(Continued)

(52) U.S. Cl.
CPC ....... *C12Q 1/6874* (2013.01); *G01N 27/4145* (2013.01); *H01L 21/02532* (2013.01);
(Continued)

(58) Field of Classification Search
CPC .......... C12Q 1/6874; H01L 21/823487; H01L 21/823475; H01L 21/823437;
(Continued)

(56) References Cited

U.S. PATENT DOCUMENTS

| 8,698,481 B2* | 4/2014 | Lieber .................... B82Y 15/00 |
| | | 257/253 |
| 2004/0110277 A1 | 6/2004 | Maeda |
| 2006/0141474 A1 | 6/2006 | Miyahara et al. |
| 2010/0327847 A1* | 12/2010 | Leiber et al. ................. 324/71.1 |
| 2011/0133255 A1 | 6/2011 | Merz |

FOREIGN PATENT DOCUMENTS

| JP | 2005-077210 A | 3/2005 |
| JP | 2009-250611 A | 10/2009 |

(Continued)

OTHER PUBLICATIONS

Burkhardt et al (Advanced Materials, 22(23) pp. 2525-2528.*

(Continued)

*Primary Examiner* — Sally A Merkling
(74) *Attorney, Agent, or Firm* — Miles & Stockbridge, P.C.

(57) ABSTRACT

In the field of the next generation DNA sequencer, a method for integrating very high sensitive FET sensors having side gates and nanopores as devices used for identifying four kinds of base and for mapping the base sequence of DNA without using reagents, and a semiconductor device having selection transistors and amplifier transistors respectively corresponding to the FET sensors having side gates and nanopores respectively so as to be able to read the variation of a detection current based on the differences among the charges of the four kinds of base without deteriorating the detection sensitivity of the FET sensor, are presented.

7 Claims, 22 Drawing Sheets

(51) Int. Cl.
*H01L 29/66* (2006.01)
*G01N 27/414* (2006.01)
*H01L 21/02* (2006.01)
*H01L 21/283* (2006.01)
*H01L 21/306* (2006.01)
*H01L 21/8234* (2006.01)

(52) U.S. Cl.
CPC ...... *H01L 21/02595* (2013.01); *H01L 21/283* (2013.01); *H01L 21/30604* (2013.01); *H01L 21/823412* (2013.01); *H01L 21/823418* (2013.01); *H01L 21/823437* (2013.01); *H01L 21/823475* (2013.01); *H01L 21/823487* (2013.01); *H01L 29/4908* (2013.01); *H01L 29/66787* (2013.01)

(58) Field of Classification Search
CPC ..... H01L 21/823418; H01L 21/823412; H01L 21/30604; H01L 21/283; H01L 21/02595; H01L 21/02532; H01L 29/66787; H01L 29/04; H01L 29/4908; G01N 27/4145
See application file for complete search history.

(56) References Cited

FOREIGN PATENT DOCUMENTS

| | | |
|---|---|---|
| JP | 2012-202864 A | 10/2012 |
| WO | WO 2003/087796 A1 | 10/2003 |
| WO | WO 2009/035647 A1 | 3/2009 |
| WO | WO 2010/020912 A1 | 2/2010 |

OTHER PUBLICATIONS

Lagerqvist, J. et al.; "Fast DNA Sequencing via Transverse Electronic Transport"; *Nanoletters*, vol. 6; No. 4; pp. 779-782; (2006).

Gierhart, B. et al.; "Nanopore with transverse nanoelectrodes for electrical characterization and sequencing of DNA"; *Sensors and Actuators* B 132; pp. 593-600; (2008).

Majkusiak, B. et al.; "Semiconductor Thickness Efffects in the Double-Gate SOI MOSFET";, IEEE Transaction on Electron Devices, vol. 45; No. 5; (1998).

* cited by examiner

CROSS-SECTIONAL VIEW TAKEN ALONG LINE A-A'

CROSS-SECTIONAL VIEW TAKEN ALONG LINE B-B'

SEMICONDUCTOR DEVICE AND MANUFACTURING METHOD THEREOF

TECHNICAL FIELD

The present invention relates to a technology regarding a sensor using a semiconductor that is a device used for identifying four kinds of base of DNA and for mapping the base sequence of DNA.

BACKGROUND ART

Since the successful mapping of the human genome, the read speed of a DNA sequencer (a device that automatically reads base sequences) has been rapidly improved. Even in the fields of molecular biology and medical care, it is expected that the further improvement of the function of a DNA sequencer will lead to successful outcomes in applications to many directions.

As approaches to realize a third-generation DNA sequencer, measurement methods, in which a nanopore device that includes a pore the size of which is almost equal to that of DNA and electrodes on both sides of the pore is used, have drawn much attention (Non-patent Literature 1). To cite an example, there is one of the measurement methods in which bases are slid one by one between electrodes on the both sides of a pore when DNA passes through the pore, and the base sequence is mapped by observing the variation of tunnel current flowing between the electrodes o the both sides of the pore. The feature of this method (referred to as a tunnel current method hereinafter) lies in the fact that the base sequence of DNA can be analyzed without labeling the DNA, that is to say, without using reagents such as enzymes and fluorescent dyes. Therefore, a process for using reagents can be omitted, with the result that it can be expected that the reduction of analysis cost and the improvement of read throughput will be achieved.

Because of improving mechanical strength in the manufacture of a nanopore device, methods, in which semiconductor substrates, semiconductor materials, and semiconductor processes are used, have drawn much attention (Non-patent Literature 2). As one of typical manufacturing methods, as disclosed in "Brian C. Gierhart, et al., "SENSORS AND ACTUATORS" B 132 (2008) 593-600", there is a method in which an insulating thin film region is deposited on a semiconductor substrate, two electrodes are formed therein, and a pore is formed by irradiating an electron beam between the two electrodes. A microscopic pore with its diameter 10 nm or less can be formed by controlling the energy of the electron beam, an irradiated area, and a current.

The tunnel current method has a problem in that a minute gap has to be provided between a pair of electrodes. According to "Johan Lagerqvist, et al., "NANO LETTERS" (2006) Vol. 6, No. 4 779-782", it is suggested that, if a gap between electrodes is set to about 1.25 nm, it becomes possible to identifying individual bases. This is because, due to the fact that the diameter of DNA is about 1 nm, if a gap with its width about 1.25 nm is not provided, it is difficult to flow a tunnel current. In patterning using semiconductor processes, it is difficult to fabricate two electrodes that have about 1.25 nm gap therebetween with high accuracy and reproductivity.

In addition, as materials for the electrodes, precious metals such as gold are mainly examined. In the tunnel current method in which the edges of electrodes are exposed, because oxidization of the edges of electrodes decreases the value of the tunnel current significantly, precious metals such as gold atoms that are oxidation resistant are required as materials for the electrodes. Furthermore, because the edges of electrodes are also exposed to a solution, precious metal electrodes such as gold electrodes are required in terms of corrosion resistance. However, because precious metals such as gold atoms are unworkable, these metals are usually not treated in semiconductor processing, and as can be seen from the fact that precious metals are usually treated as metallic pollution sources in the semiconductor line of an LSI semiconductor process, precious metals have low affinities for the semiconductor processing.

In addition, according to "Johan Lagerqvist, et al., "NANO LETTERS" (2006) Vol. 6, No. 4 779-782", as for the thickness of the electrode, it is indicated that the bases can be identified from one another with an assumption that the edge of the electrode is equal to 3×3 gold atoms. This assumption is adopted in consideration the fact that, because the pitch of each base of DNA is about 0.34 nm, if the thickness of the electrode is larger than 0.34 nm, tunnel currents that flow through plural bases are detected at the same time, and therefore it becomes impossible to measure the base sequence. Generally speaking, however, it is difficult to form an electrode (especially a gold electrode) in the form of a thin film with its thickness 5 nm or below. When a thin film with its thickness 5 nm or below is attempted to be formed, it becomes difficult because a substance, with which the thin film is attempted to be formed, becomes energetically stabler when the substance is in a dot state than in a thin film state. Especially, it is almost impossible to form an electrode of a thin film whose thickness is comparable with the resolution ability of one base (0.34 nm).

Furthermore, a gold electrode is more susceptible to the reposition of atoms and electromigration at the time of voltage application than electrodes made of other metals. Therefore, the accuracy of measurement results is deteriorated due to the fluctuations of gold atoms at the time of detecting tunnel currents.

CITATION LIST

Non-Patent Literature

Non-patent Literature 1: Johan Lagerqvist, et al., "NANO LETTERS" (2006) Vol. 6, No. 4 779-782

Non-patent Literature 2: Brian C. Gierhart, et al., "SENSORS AND ACTUATORS" B 132 (2008) 593-600

Non-patent Literature 3: Bogdan Kajkusiak, et al., "IEEE TRANSACTION ON ELECTRON DEVICES", VOL 45, NO. 5, May 1998

SUMMARY OF INVENTION

Technical Problem

In order to solve the problem described in BACKGROUND, the inventors have devised the following sensor configuration. The sensor will be referred to as a nanopore FET sensor 100 or a pore FET sensor 100 hereinafter in the present specification. The configuration of the sensor is a configuration shown in FIG. 1A to FIG. 1C. Reference numeral 108 denotes an insulating film; 101 denotes a channel; 102 denotes a control gate; 103 denotes a source; 104 denotes a drain; 105 denotes a back gate; 106 denotes a pore (nano-sized minute hole); and 107 denotes a wiring used for a contact to the control gate 102, the source 103, the drain 104, or the back gate 105. The pore 106 resides between a side face of the control gate 102 fronting onto the channel 101 and a side face of the channel 101 fronting onto the control gate 102 (refer to FIG. 1A); on an edge of the channel 101 fronting onto the control gate 102 (refer to FIG. 1B); or in the channel 101 near to the side face of the channel 101 fronting onto the control gate 102 (refer to FIG. 1C).

FIG. 2 is an enlarged view of the vicinity of the pore 106. As shown in FIG. 2, when the nanopore FET sensor is soaked in a solution including a biological material that is an object to be examined, the DNA (200) of the object to be examined passes through the pore (a series of blocks of the DNA (200) represents a series of bases).

When voltages are applied to the source 103 and the drain 104 so that the source voltage<the drain voltage, this device works as a transistor by controlling the voltage of the control gate. This device is a so-called side-gated transistor. When the transistor is on, because an inversion layer is induced on the side portion of the channel fronting onto the control gate (fronting onto the pore), the current flows through the side portion of the channel fronting onto the control gate. Although the thickness of the inversion layer partly depends on the control gate voltage, it is usually very thin, and about 2 to 3 nm or less.

The channel current varies in accordance with the variation of the electric field caused by the differences between effective electric charges and effective electric fields of the nucleotides of four kinds of base of DNA passing through the pore 106, with the result that the identification of the four kinds of base and the mapping of the base sequence can be performed by detecting the variation of the channel current. Because the widths of gaps among the arrayed bases of DNA are about 0.34 nm, it is necessary that the thickness of the current flowing through the side portion of the channel 101 should be made as thin as possible, so that a current due to the variation of the electric field induced by one base unit (in units of one nucleotide) can be detected. For that purpose, it is necessary that the thickness of the channel 101 should be made thin.

In Non-patent Literature 3, the electron density distribution in silicon which is sandwiched in between insulating films ($SiO_2$) is calculated. Especially as is clear from FIG. 4 in Non-patent Literature 3, when the thickness of the silicon is 10 nm or below, electron densities are located around the center. Especially, when the thickness of the silicon region becomes 5 nm or below, then the value of the current is mainly affected by one base (one nucleotide) that comes to the position showing the peak of the electron density distribution, and the peak of the electron density distribution becomes sharper. Therefore, the identification ability of the size of about one base can be obtained. In addition, in the scope of the thickness of the silicon region being 5 nm or below, fundamentally it becomes difficult for two or more electrons to reside together in the direction of the thickness of the channel.

FIG. 3A is a schematic view showing the existence probability of one electron in silicon sandwiched in between $SiO_2$, and FIG. 3B is a schematic view showing the existence probabilities of two electrons in silicon sandwiched in between $SiO_2$. When the thickness of the channel becomes 5 nm or less, the difference between the energy of the system shown in FIG. 3A and the energy of the system shown in FIG. 3B becomes equal to or larger than room energy ($k_BT$). The energy state of FIG. 3B has a larger amount of energy than the energy state of FIG. 3A has. Accordingly, an electron supplied from a source can exist only in the state shown in FIG. 3A, that is to say, in the state in which only one electron can exist, in the direction of the thickness of the channel, and therefore a resolution ability equivalent to one electron unit can be obtained. Consequently, in order to obtain sufficient detection sensitivity, it is desirable that the thickness of the channel should be 5 nm or less.

On the basis of the above described configuration and behavior, a pseudo-one dimensional narrowest current path can be formed in the side wall portion of the thin film channel with the use of an inversion layer effect and a locked-in effect to a quantum well in the direction of the thickness. Thanks to the pseudo-one dimensional narrowest current path, a current flowing through the current path sensitively reacts to a fine variation of the electric field induced by an object to be examined in the pore. Therefore, the variation ratio of the detection signal (detection sensitivity) can be increased.

The current flowing through the channel 101 is the flow of electrons induced by an electric field generated from the control gate 102. Therefore, it is desirable that the pore 106 should be disposed between the control gate 102 and the current path of the channel 101. With this disposition of the pore 106, the potential variation induced by the object to be examined in the pore modulates an electric field between the control gate and the channel in a very effective way, and the variation of the electric field can be reflected in the channel current. The nearer to the current path, which is inside the channel adjacent to the side portion of the channel, the pore 106 is, the more remarkably the detection sensitivity can be improved. One of configurations that provide the most excellent detection sensitivity is a configuration in which the pore 106 is located at a position extremely near to the side portion of the channel 101, or a configuration in which the pore 106 is formed inside the channel adjacent to the side portion of the channel 101 as shown in FIG. 1B and FIG. 10 respectively.

Furthermore, in order to form a stable one-dimensional electron conduction path, which is located more nearer to the side portion of the channel, by suppressing the spread of the current path in the width direction of the channel more effectively, it is effective to apply a voltage to the back gate 105 and to control an electric field so that electrons are concentrated toward the control gate.

In order to improve the throughput of measurement using the above described devices (nanopore FET sensors 100), it is desired that the sensors should be integrated into an LSI circuit.

In the integration of the above devices, if wirings are pulled out from the source, drain, and gate of each sensor respectively, the integration efficiency is extremely low when the improvement of the integration efficiency (the increase of the number of sensors per unit area) is taken into consideration. Therefore, it is conceivable that an area occupied by the wirings is brought down by sharing sharable wirings. In this instance, an array configuration as shown in FIG. 4A is usually conceived. FIG. 4A shows a sensor array including 2×2 sensors as an example. To put it concretely, wirings (L5 to L8) that connect control gates and back gates in a row direction are shared respectively, and wirings that connect sources and drains in a column direction are shared respectively. Successively, in the case where signals in the upper row are read out (selected), if the nanopore FET sensors are formed using NMOS, by setting the gate voltages of L5 and L6 higher than the voltages of L1 to L4, and by preparing the voltage difference between the voltage of L1 and that of L2 and the voltage difference between the voltage of L3 and that of L4, currents flow through the channels of the nanopore FETs. Herewith, DNA can be detected, and the currents are transmitted to peripheral circuits (to an amplifier unit, and the like) through the wirings of L1 and L3. On the other hand, in the nanopore FET sensors in the lower row, the voltages applied to L7 and L8 are set lower than the voltages applied to L1 to L4 so that channel currents do not flow (deselected). With such a configuration as above, only signals from the sensors disposed in the upper row can be detected. After the signals of the sensors in the upper row are detected, the nanopore FETs in the lower row are set selective, while the nanopore FETs in the upper row are set deselective. With such a setting as above, signals detected by the sensors disposed in the lower row can be detected. By repeating the above operation at a high speed, the parallel measurement of objects to be examined can be performed with the use of the integrated circuit including four sensors. By expanding the block including 2×2 sensors into a block including N×N sensors, the parallel measurement of the N×N sensors can be performed.

On the other hand, a nanopore FET sensor 100 has a problem. FIG. 5 shows an experimental result showing the control gate voltage dependence characteristics of the channel currents of NMOS type nanopore FET sensors. Transistor characteristics that the channel currents of nanopore FET sensors begin to flow or begin to increase by raising their respective gate voltages can be checked. In FIG. 5, the absolute values of a source current and a drain current for each of different chips are superimposingly drawn. FIG. 5 is a diagram showing the transistor characteristics of different nanopore FET sensors that are designed in the same way. By comparing the transistor characteristics of Chip A, Chip B, and Chip C with one another, it is clear that the channel currents of the respective chips have different control gate voltages (threshold voltages) at which the respective channel currents begin to flow. According to the result of examination of the trial products of nanopore FET chips, it has become apparent that the variations of threshold voltages are extremely large. The transistor characteristics shown in FIG. 5 are some examples, and there are many other chips among chips manufactured in the same process that have thresholds lower than the threshold of any of Chip A to Chip C, or that have thresholds higher than the threshold of any of Chip A to Chip C. In other words, there exists a nanopore transistor that does not turn on or off without an unrealistic voltage applied to its gate.

As a result of earnestly studying and examining the cause for the above variations of the thresholds, the cause is considered as follows.

Because a nanopore FET is a transistor with a thin channel, and its current path concentratedly exists near the side face of the channel fronting onto its control gate, a pseudo-one dimensional narrow current path flows through the side face of the channel. Therefore, if a fixed charge exists in an insulating film near to the side face of the channel or on the surface of the interface between the insulating film and the channel, the variation of the threshold of the nanopore FET becomes very large depending on the amount and location of the fixed charge. The reason why the variation becomes very large will be explained using FIG. 6A and FIG. 6B. Reference numeral 502 in FIG. 6A or FIG. 6B denotes the side wall portion of the channel. Furthermore, reference numeral 501 denotes a fixed charge existing in an insulating film near to the side wall of the channel or on the surface of the interface between the insulating film and the channel. In addition, arrows in FIG. 6A and FIG. 6B denote the flows of currents. Here, in the case of assuming that the fixed charge is a negative charge and the nanopore FET is a NMOS type nanopore FET, it becomes difficult for currents to flow around the fixed charge, so that the currents flow as shown in FIG. 6A or FIG. 6B in such a way that the currents get around the fixed charge. In the case where the thickness of the channel is thick (as shown in FIG. 6A), although the currents flowing around the fixed charge are affected by the fixed charge, currents far from the fixed charges are not affected so much by the fixed charge. Therefore, in this case, the shift value of the threshold of the transistor due to the fixed charge is small. On the other hand, in the case where the thickness of the channel is thin (as shown in FIG. 6B), because most currents passing through the channel are affected by the fixed charge, the variation of the threshold voltage due to the fixed charge becomes large. Therefore, the variation of the amount and location of the fixed charge largely affect the variation of the threshold voltage.

Generally speaking, a side-gate transistor has an insulating film deposited by a CVD method on an insulating film between a gate and a channel (in the case of a transistor having a gate over a channel, an insulating film between a gate and a channel is a thermally-oxidized film), and the insulating film deposited by a CVD method has a larger amount and a larger variation of a fixed charge than a thermally-oxidized film has. Furthermore, because a nanopore FET itself is a transistor having a pore near to its channel, the side wall of the pore, nearby unattached bonds, and the like are causative agents for generating a fixed charge, with the result that the variation of the amount and location of the fixed charge becomes large. Therefore, the variation of the threshold of this sensor becomes very large.

The above-described problem unique to a nanopore FET has become clear for the first time from the result and the examination of this experiment.

When such nanopore FET sensors as above are integrated as shown in FIG. 4A, there occurs a problem in that a sensor having a low threshold voltage and a poor off characteristic is produced. Even if a voltage, which is set as an off voltage, is applied to such a sensor in order to set the sensor deselective, the sensor does not become off, and a leakage current flows from the sensor. This leakage current is mixed with signals output from selected sensors, and therefore it becomes a cause for noise generation.

Because the nanopore FET sensor has a thin film channel, the values of detection currents are small. Additionally, it is necessary to distinguish much smaller differences among signals of four kinds of base out of the small detection currents. Therefore, noises due to the leakage currents from the deselected cells severely deteriorate the accuracy of signal analysis.

Consequently, a problem to be solved is how to read detection currents from selected sensors while cutting off causes for noise generation when nanopore FET sensors are fabricated in the form of an LSI.

Solution to Problem

In order to solve the above problem, the present invention proposes a semiconductor device wherein a source, a drain, and a channel connecting the source and the drain are formed on an insulating film, a control gate is or a control gate and a back gate are formed fronting onto one side face of the channel or formed fronting onto both side faces of the channel via the insulating film, and a plurality of sensors are disposed, the sensors having a nano-sized pore through which an object to be examined passes and that is formed near to the side face of the channel fronting onto the control gate through the insulating films, the semiconductor device including plural selection transistors, each of which is capable of electrically selecting or deselecting the detection signal output of the relevant sensor.

In addition, in order to solve the above problem, the present invention proposes the semiconductor device configured in such a way that plural combination circuits, each of which includes one selection transistor connected to the source of one sensor outputting a channel current on a one-to-one basis, are disposed in an array configuration.

Furthermore, in order to solve the above problem, the present invention proposes the semiconductor device configured to further include amplifier transistors the gate of each of which is connected to the source of one of the sensors outputting a channel current and to a constant voltage source via a resistor, wherein plural combination circuits, each of which includes one amplifier transistor and one selection transistor that are connected to each other and further includes one sensor connected thereto, are disposed in an array configuration.

In addition, in order to solve the above problem, the present invention proposes the semiconductor device configured in such a way that plural sensors are disposed in an array configuration; the selection transistors are each prepared for each row of the sensor array; the drains of all the sensors disposed in each row are connected in common to the relevant selection transistor disposed in the row; a selection voltage is applied to the gates of selection transistors in a row to be selected; a deselection voltage is applied to rows other than the row to be selected; and herewith a configuration for performing control to obtain sensor signals for each row is realized.

Furthermore, in order to solve the above problem, the present invention develops a manufacturing method of a semiconductor device that includes the steps of: depositing an insulating film on a semiconductor substrate; forming a source region, a drain region, a control gate region, and a back gate region of a sensor by depositing polysilicon on the insulating film and patterning the polysilicon; forming a channel of the sensor by depositing nondoped polysilicon and patterning the nondoped polysilicon; performing etching to form a region in which a selection transistor is formed after depositing an insulating film; forming the source region and the drain region of the selection transistor by depositing polysilicon and patterning the polysilicon; forming a channel of the selection transistor by depositing nondoped polysilicon and patterning the nondoped polysilicon; forming a gate insulating film of the selection transistor by thermal oxidation; forming a gate electrode of the selection transistor by depositing polysilicon and patterning the polysilicon; forming an interlayer film, and wirings from individual electrodes; and etching the insulating film over the vicinity of a place where a nanopore is to be formed, and etching the semiconductor substrate at the back side to finally form a nanopore in the vicinity of the channel of the sensor by etching.

Advantageous Effects of Invention

Briefly explaining, an advantageous effect obtained by a typical aspect of the present invention disclosed in this application is as follows. Identification of four kinds of DNA base and identification of the base sequence of DNA can be performed with a high degree of accuracy.

DESCRIPTION OF EMBODIMENTS

Figure 1A:
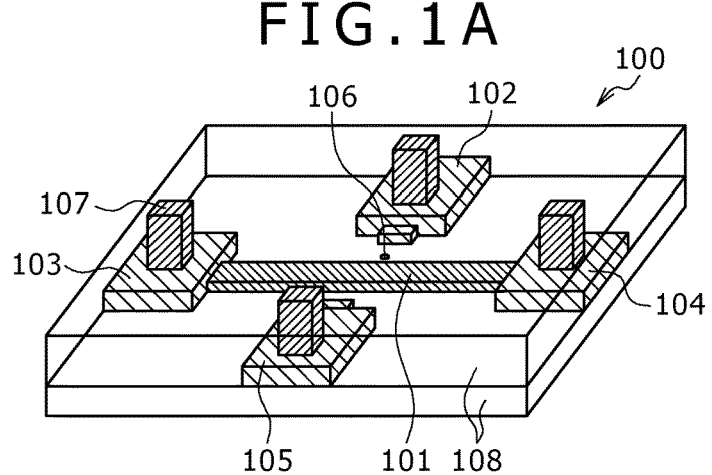
FIG. 1A is a schematic view of the first configuration of a nanopore FET sensor proposed by the present invention.
Figure 1B:
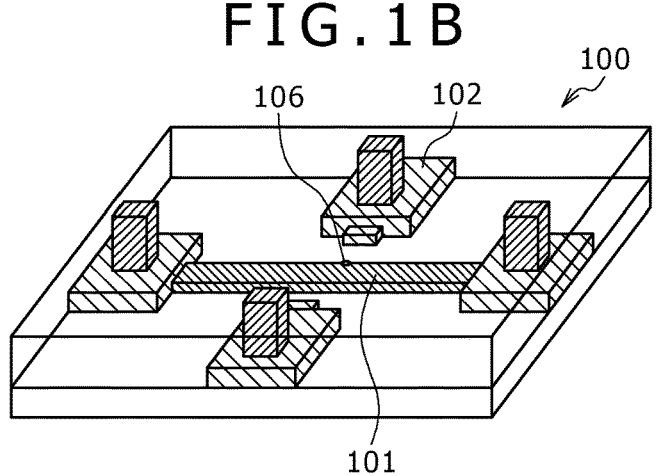
FIG. 1B is a schematic view of the second configuration of a nanopore FET sensor proposed by the present invention.
Figure 1C:
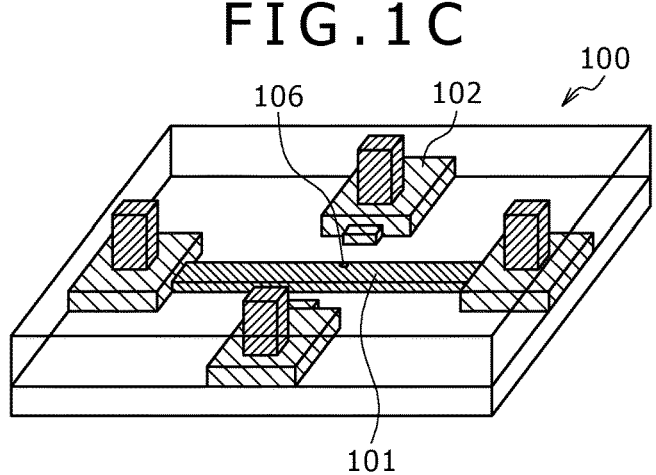
FIG. 1C is a schematic view of the third configuration of a nanopore FET sensor proposed by the present invention.
Figure 2:
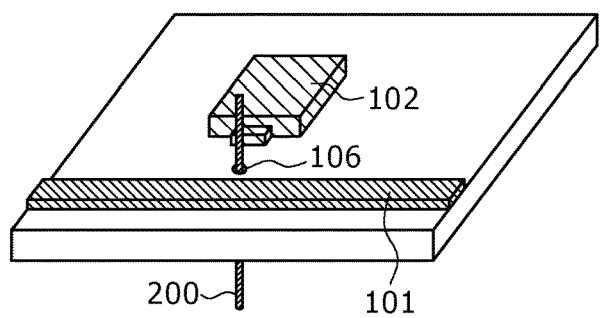
FIG. 2 is an enlarged schematic view of the vicinity of a pore of a nanopore FET sensor proposed by the present invention.
Figure 3A:
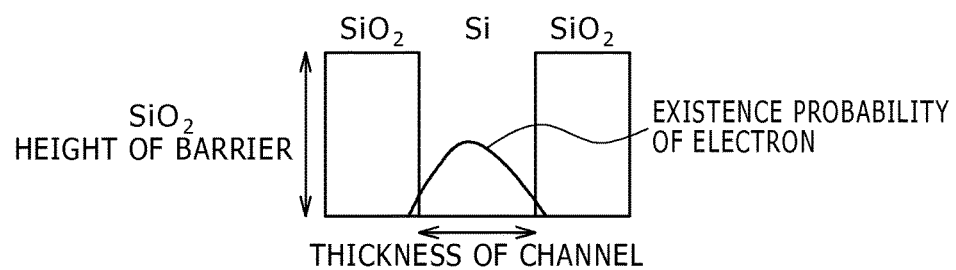
FIG. 3A is a schematic view showing the existence probability of one electron in a silicon region sandwiched in between $SiO_2$.
Figure 3B:
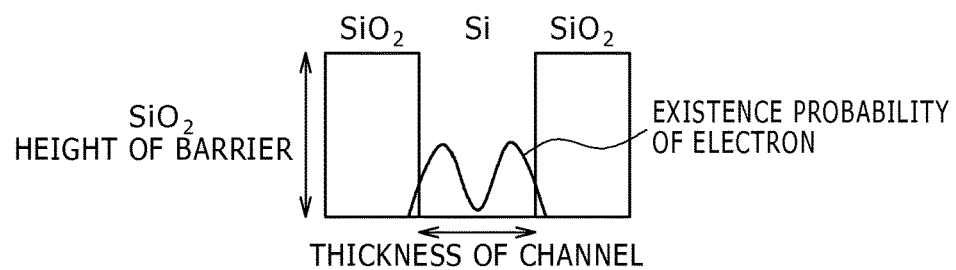
FIG. 3B is a schematic view showing the existence probabilities of two electrons in a silicon region sandwiched in between $SiO_2$.
Figure 4A:
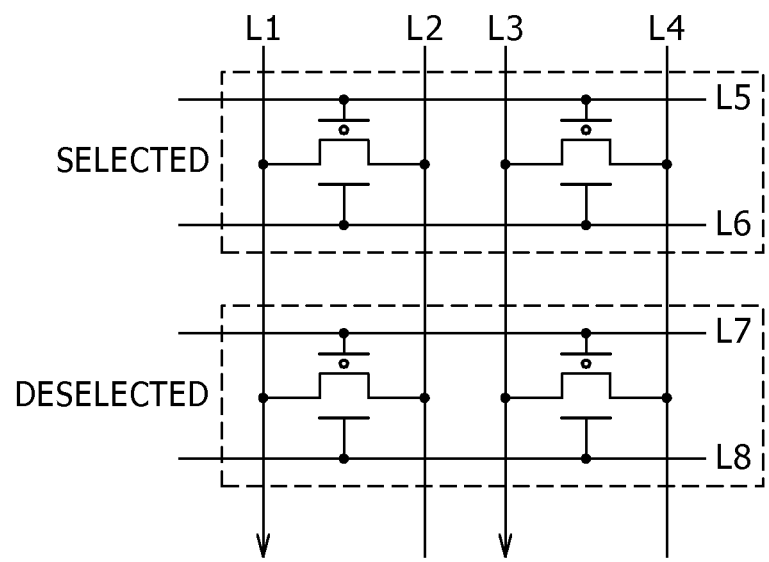
FIG. 4A is a circuit diagram for explaining an example of an array configuration of nanopore FET sensors proposed by the present invention.
Figure 4B:
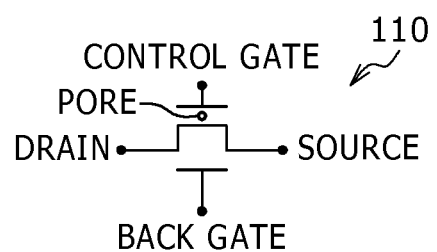
FIG. 4B is a circuit diagram showing a nanopore FET sensor cell proposed by the present invention.

Throughout all the drawings for explaining the embodiments of the present invention, elements having the same functions will be denoted by the same reference numerals, and redundant description thereof will be omitted as much as possible. Hereinafter, the embodiments of the present invention will be described in detail with reference to the accompanying drawings. Device configurations and materials described in the embodiments are examples for materializing the concept of the present invention, and these configurations and materials do not strictly specify materials and dimensions.

First Embodiment

In order to solve the above described problem, it is effective that a switching element is installed in series with the source, which emits the channel current of a nanopore FET sensor (hereinafter, a nanopore FET sensor integrated on a semiconductor chip as a cell unit will be referred to as a nanopore FET), and the integrated nanopore FET 110 is selected or deselected by switching the switching element on or off. Although the following embodiments give descriptions with back gates, it is effective even without a back gate.

Figure 7:
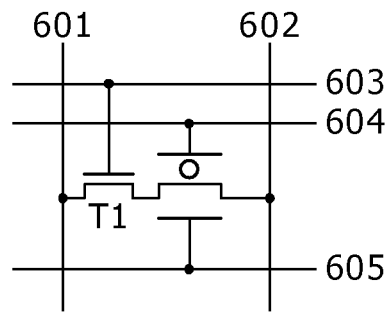
FIG. 7 is a diagram for explaining the circuit to which a selection transistor of a first embodiment is added.

FIG. 7 is a diagram showing a part of a circuit of a first embodiment of the present invention.

In FIG. 7, reference numeral T1 denotes a selection transistor; 601 denotes a read line (bit line); 603 denotes a wiring for applying a voltage to the gate of the selection transistor (word line); 602, 604, and 605 denote wirings for applying voltages to the drain, the control gate, and the back gate of the nanopore FET respectively.

Figure 8:
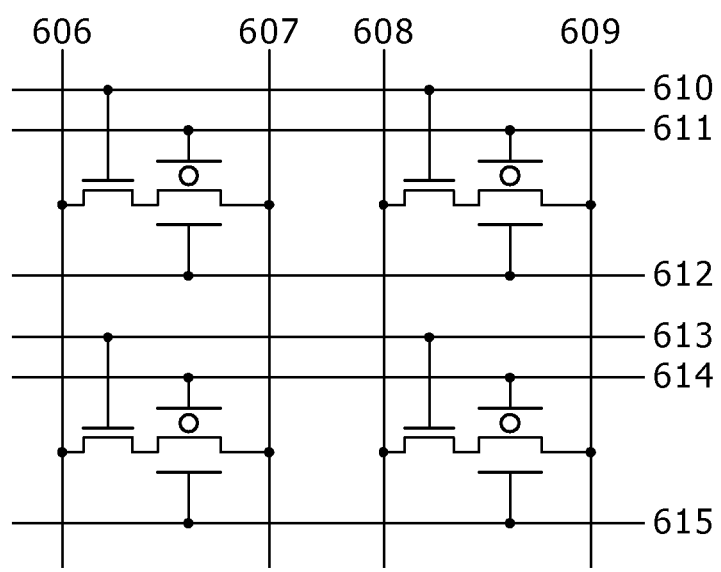
FIG. 8 is a diagram for explaining an example of arraying the circuit shown in FIG. 7 of the first embodiment.

As the selection transistor, not a transistor having a large variation of its threshold, but a normally configured FET having a gate just over an insulating film (referred to as a vertical gate FET in this specification hereinafter) will be used. A vertical gate FET is extremely reliable, has a good off characteristic, and has a small variation thanks to its already-matured semiconductor processing, and therefore it is the most suitable to be used as a selection transistor. FIG. 8 is a diagram showing a 2-by-2 array as an example of a circuit made by arraying circuits each of which is equivalent to the circuit shown in FIG. 7. It goes without saying that this 2-by-2 array can be expanded into a generic N-by-N array.

Explanation of the behavior of the circuit of this embodiment will be made using FIG. 8. First, a behavior in the case where the upper row is selected, and the lower row is deselected will be described. In this specification, description will be made under the assumption that all the FETs including nanopore FETs are NMOS FETs. The relation between the voltages of the wirings 606 and 607 is set so that the voltage of the wiring 606<the voltage of the wiring 607; the relation between the voltages of the wirings 608 and 609 is set so that the voltage of the wiring 608<the voltage of the wiring 609; the voltage of the wiring 610 is set higher than the voltages of the wirings 607 and 609, and the voltage of the wiring 611 is set higher than the voltages of the wirings 607 and 609. With the above setting, detection currents flow through the channels of nanopore FETs and the channels of selection transistors in the upper row, and these currents flow to peripheral signal processing circuits through bit lines 606 or 608. On the other hand, the voltage of the wiring 613 is set lower than the voltages of the wirings 606 and 608 so that currents do not flow through selection transistors in the lower row. With the above setting, even if there is a nanopore FET sensor that has a low threshold and through which a leakage current flows in the lower row, a selection transistor belonging to the nanopore FET sensor blocks the leakage current, and therefore only the detection currents flowing the sensors in the upper row can be detected without noises due to leakage currents.

Figure 9A:
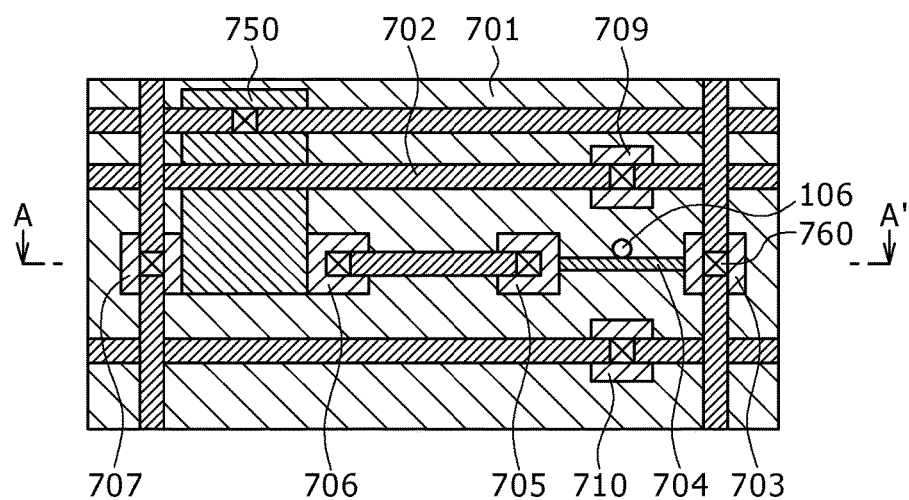
FIG. 9A shows the top view of a set of a nanopore FET and a selection transistor of the first embodiment.
Figure 9B:
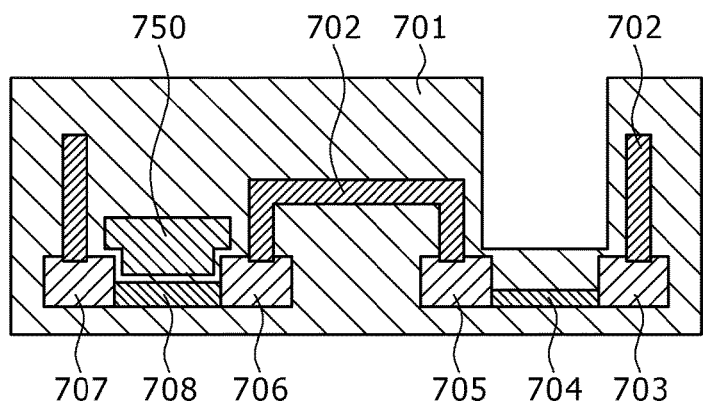
FIG. 9B shows a cross-sectional view taken along the line A-A' of FIG. 9A.

FIG. 9A shows the top view of a set of a nanopore FET and a selection transistor, and FIG. 9B shows a cross-sectional view taken along the line A-A' of FIG. 9A. In FIG. 9A, for easy understanding, an insulating film located over the channel of the nanopore FET is omitted. Reference numeral 701 denotes an insulating film; 702 denotes a wiring; 703 denotes the drain of the nanopore FET; 704 denotes the channel of the nanopore FET; 705 denotes the source of the nanopore FET; 706 denotes the drain of the selection transistor; 707 denotes the source of the selection transistor; 708 denotes the channel of the selection transistor; 709 denotes the control gate of the nanopore FET; 710 denotes the back gate of the nanopore FET; 750 denotes the gate of the selection transistor; 760 denotes a contact portion to a gate, a source, or a drain; and reference numeral 106 denotes a nanopore. Wirings that run vertically or horizontally are connected to the peripheral signal processing circuits while making contacts with electrodes in accordance with the circuit diagram shown in FIG. 8. When the nanopore FET sensor 100 is active, there is a solution including an object to be examined over the upper part and under the lower part of the insulating film 701 of the nanopore FET sensor FET 100, and when DNA passes through the nanopore of the nanopore FET sensor, the value of the channel current varies in accordance with the signal differences among four kinds of base, and the four kinds of base can be identified respectively by reading the variation of the value of the channel current.

As shown in FIG. 9B, a vertical gate FET, which is reliable, has just a small variation and a good off characteristic, is used as the selection transistor of the nanopore FET. In terms of the process of the nanopore FET, when a side gate transistor of the nanopore FET is formed, if the same side gate transistor is formed beside the above side gate transistor, and that is made a selection transistor, this leads to the reduction of the number of processes, resulting in a cost merit and the reduction of manufacturing time. However, as described above, it has been found that, because a side gate transistor formed on a thin film has a large variation of its threshold, it is not suitable for a side gate transistor to be used as a selection transistor. Therefore, as described in this embodiment, it is advantageous to adopt a vertical gate transistor that is highly reliable, has just a low variation, and a good off-characteristic as a selection transistor using a manufacturing process different from the manufacturing process of a nanopore FET.

An example of a manufacturing method of the nanopore FET sensor device, which has a selection transistor and is shown in FIG. 7, will be explained with reference to FIG. 14 to FIG. 27. The process flow of the nanopore FET sensor device is explained using the cross-sectional view along the line A-A' of FIG. 9B. In addition, it will be assumed that peripheral circuits, which are located outside the sensor array and handle detection signals from individual electrodes, are formed in advance before the formation of the sensor array (process to be described below).

Figure 14:
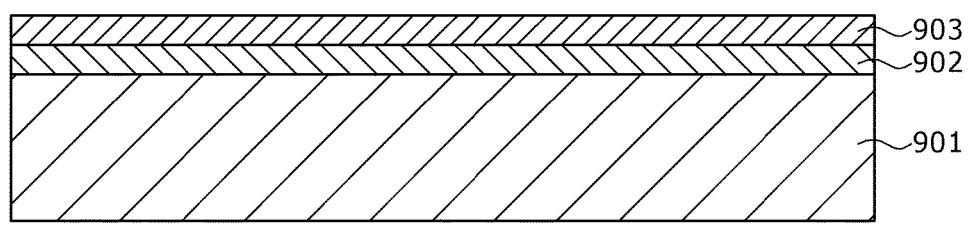
FIG. 14 is a diagram for explaining a process of the manufacturing method of a semiconductor device of the first embodiment.

(1) As shown in FIG. 14, a silicon nitride film 902 and a silicon dioxide film 903 are deposited on a silicon substrate 901 in this order.

Figure 15:
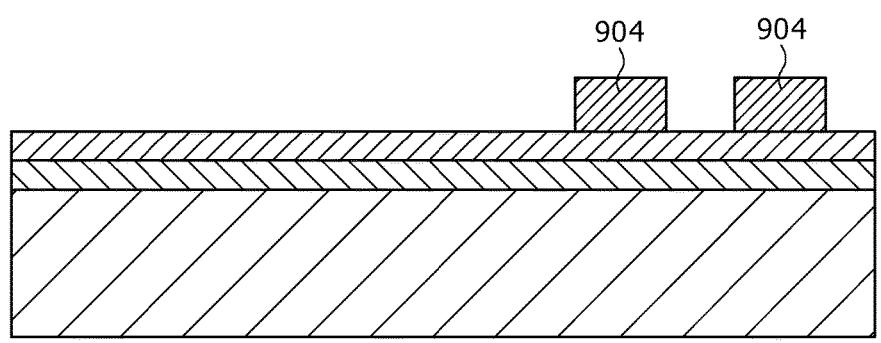
FIG. 15 is a diagram for explaining a process of the manufacturing method of the semiconductor device of the first embodiment.

(2) As shown in FIG. 15, by depositing N type polysilicon, and by patterning the deposited polysilicon, the source and drain regions 904 of the nanopore FET are formed, and the control gate region and the back gate region are formed at positions facing each other in front and behind between the source region and the drain region 904, although the control gate region and the back gate region are not shown in the figure.

Figure 16:
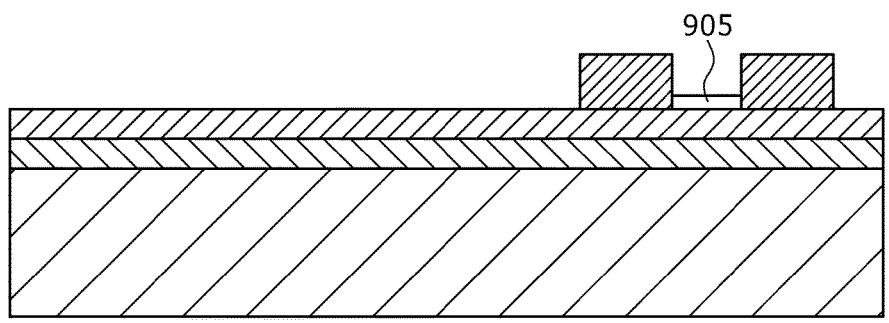
FIG. 16 is a diagram for explaining a process of the manufacturing method of the semiconductor device of the first embodiment.

(3) As shown in FIG. 16, by depositing nondoped polysilicon, and by patterning the deposited nondoped polysilicon, the channel 905 of the nanopore FET is formed.

Figure 17:
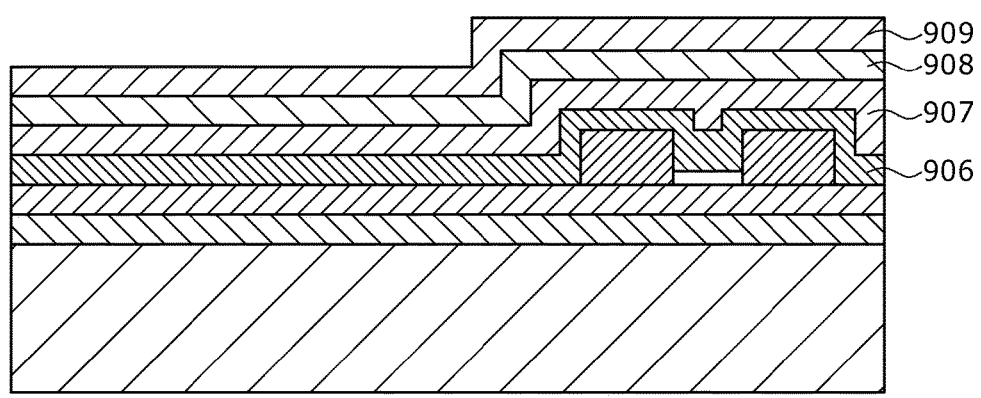
FIG. 17 is a diagram for explaining a process of the manufacturing method of the semiconductor device of the first embodiment.

(4) As shown in FIG. 17, silicon dioxide films 906 and 908, silicon nitride films 907 and 909 are deposited.

Figure 18:
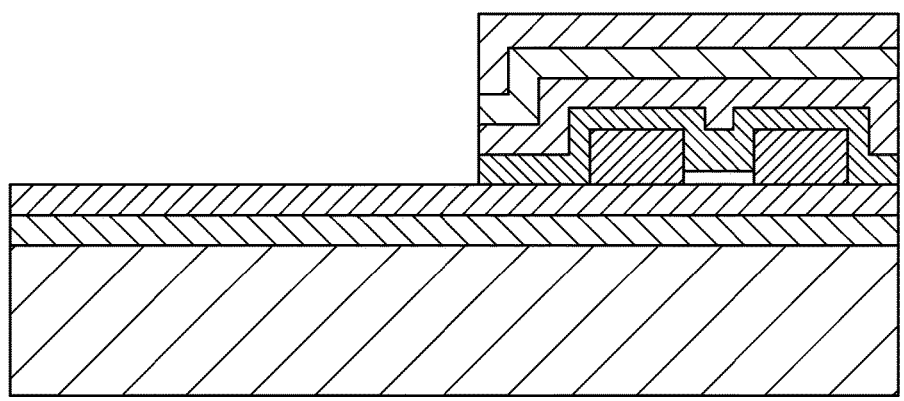
FIG. 18 is a diagram for explaining a process of the manufacturing method of the semiconductor device of the first embodiment.

(5) As shown in FIG. 18, in order to obtain a space in which a selection transistor is formed, parts of the silicon dioxide films 906 and 908, and parts of the silicon nitride films 907 and 909 are etched away.

Figure 19:
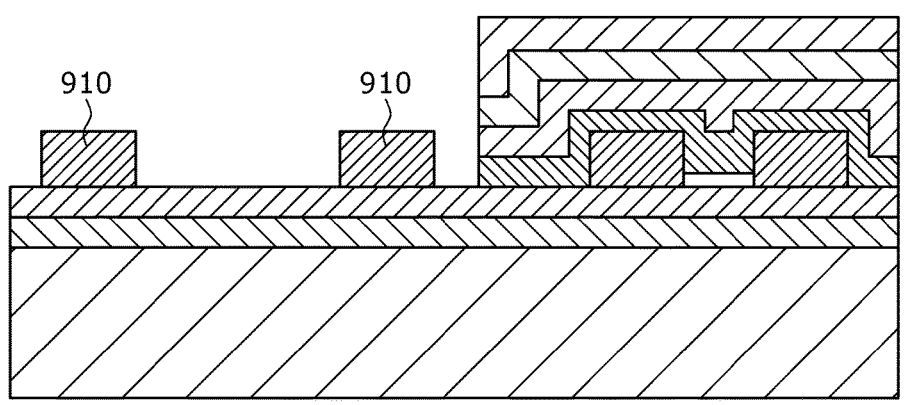
FIG. 19 is a diagram for explaining a process of the manufacturing method of the semiconductor device of the first embodiment.

(6) As shown in FIG. 19, by depositing N type polysilicon, and by patterning the deposited N type polysilicon, the source and drain regions 910 of the selection transistor are formed.

Figure 20:
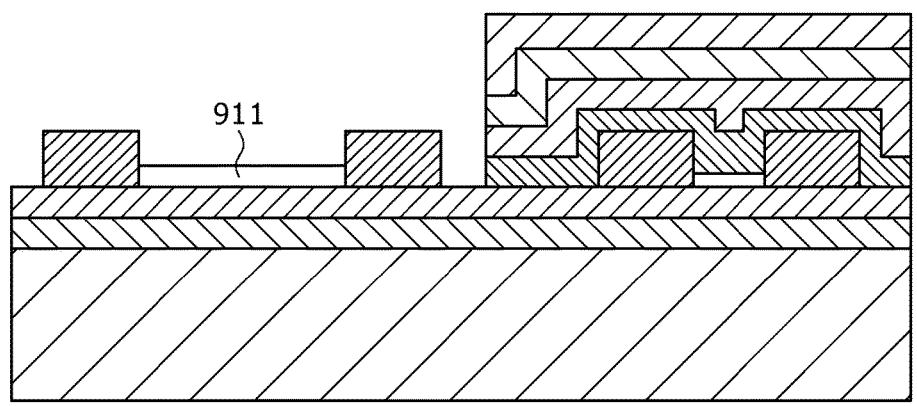
FIG. 20 is a diagram for explaining a process of the manufacturing method of the semiconductor device of the first embodiment.

(7) As shown in FIG. 20, by depositing nondoped polysilicon 911, and by patterning the deposited nondoped polysilicon 911, the channel of the selection transistor are formed.

Figure 21:
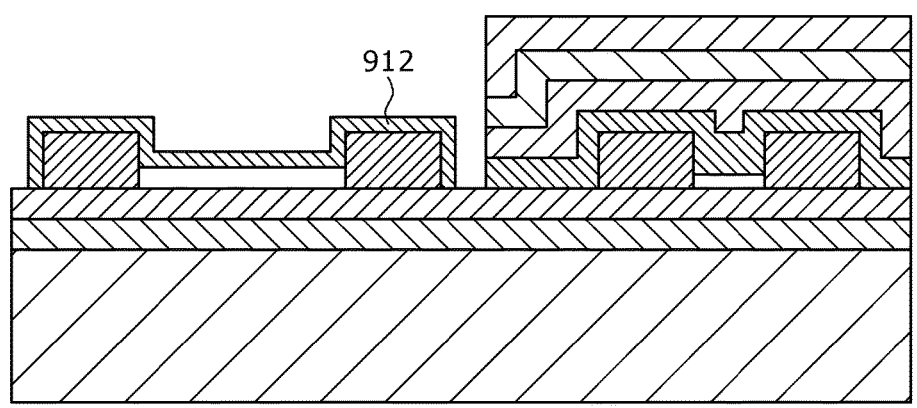
FIG. 21 is a diagram for explaining a process of the manufacturing method of the semiconductor device of the first embodiment.

(8) AS shown in FIG. 21, the gate insulating film 912 of the selection transistor is formed by thermo oxidation.

Figure 22:
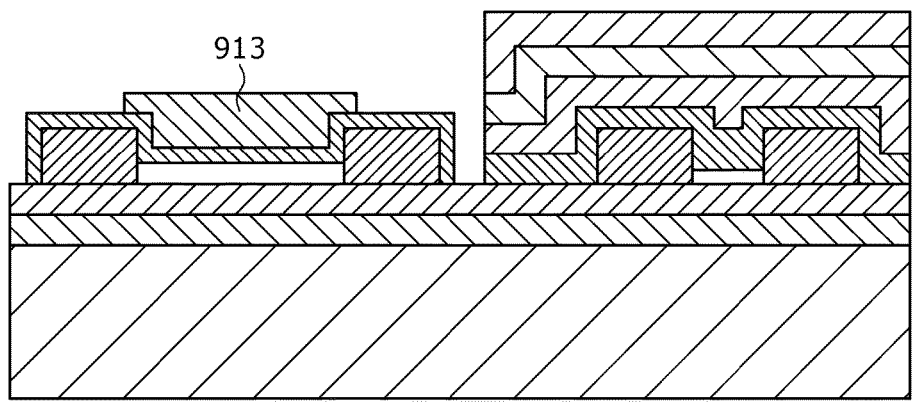
FIG. 22 is a diagram for explaining a process of the manufacturing method of the semiconductor device of the first embodiment.

(9) As shown in FIG. 22, by depositing N type polysilicon, and by patterning the deposited N type polysilicon, the gate electrode 913 of the selection transistor is formed.

Figure 23:
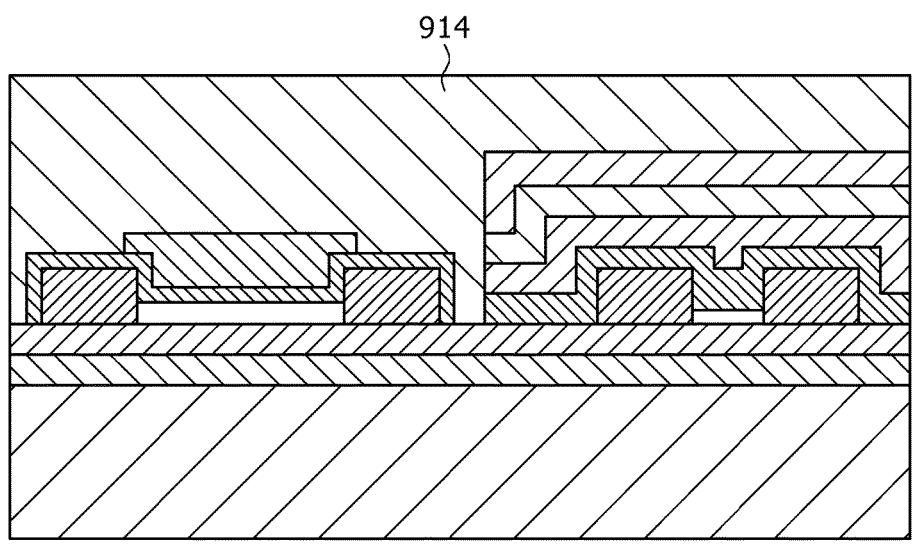
FIG. 23 is a diagram for explaining a process of the manufacturing method of the semiconductor device of the first embodiment.

(10) As shown in FIG. 23, a silicon nitride film 914 is deposited as an interlayer film, and the deposited silicon nitride film 914 is flattened using a CMP method.

Figure 24:
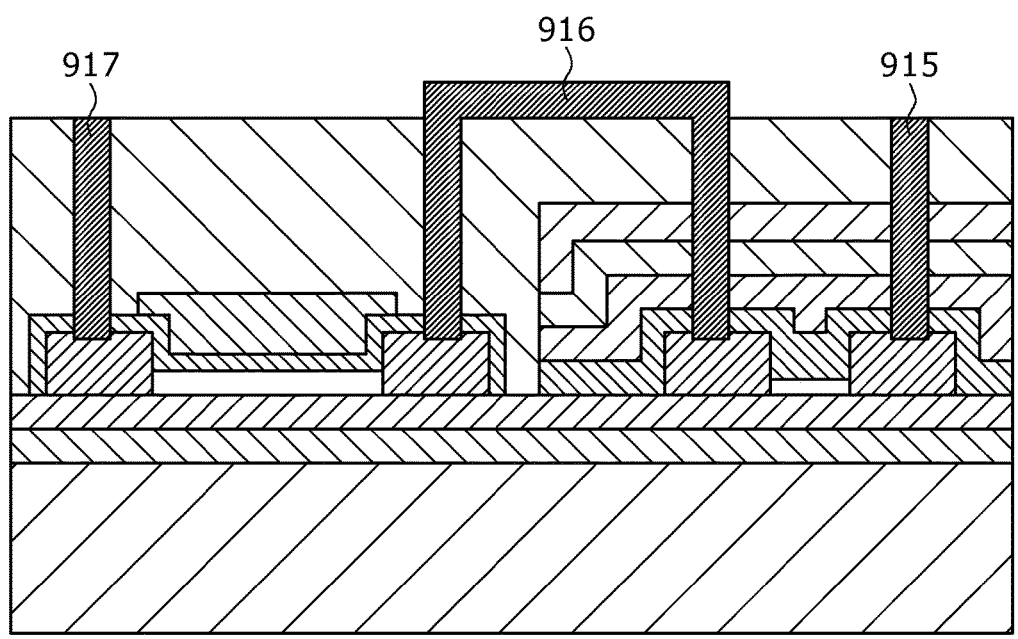
FIG. 24 is a diagram for explaining a process of the manufacturing method of the semiconductor device of the first embodiment.

(11) As shown in FIG. 24, contact holes are formed in individual electrodes of the selection transistor and the nanopore FET; wiring materials are deposited; the deposited wiring materials are flattened using the CMP method; wiring materials are deposited again; and a wiring that connects the source of the nanopore FET and the drain of the selection transistor, a wiring that connects the control gate of the nanopore FET to the peripheral circuits, a wiring that connects the back gate of the nanopore FET to the peripheral circuits, and a wiring that connects the gate of the selection transistor to the peripheral circuits are formed.

Figure 25:
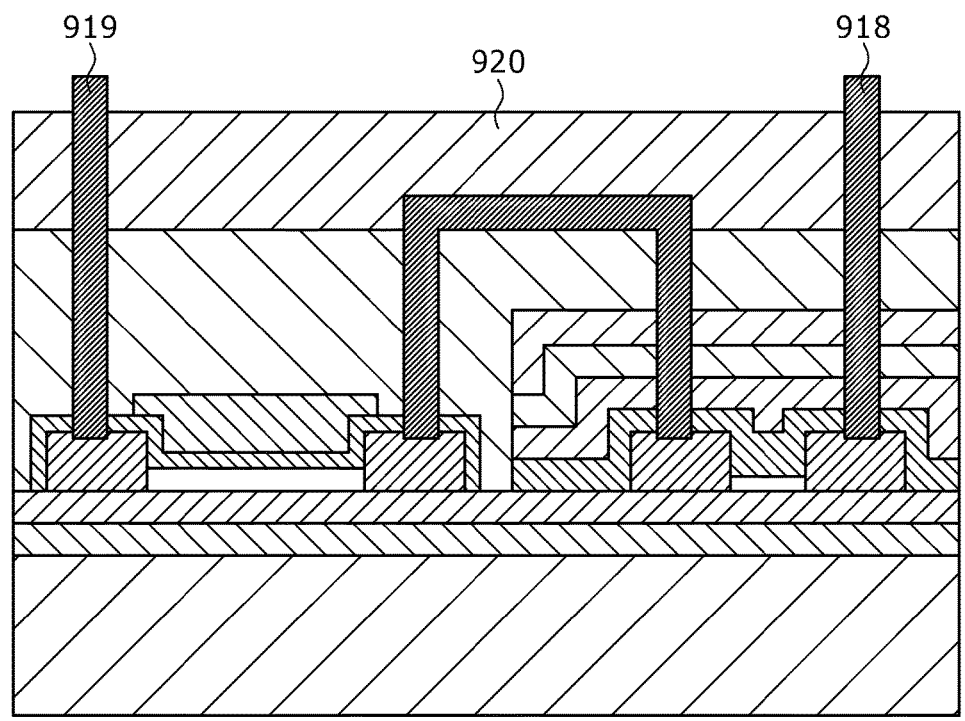
FIG. 25 is a diagram for explaining a process of the manufacturing method of the semiconductor device of the first embodiment.

(12) As shown in FIG. 25, after a silicon nitride film 920 is deposited as an interlayer film, the silicon nitride film 920 is flattened by the CMP method; apart of the insulating film on the wiring portion connected to the drain of the nanopore FET and a part of the insulating film on the wiring portion connected to the selection transistor are etched away; after wiring materials are deposited, the wiring materials are flattened by the CMP method; and afterward wiring materials are deposited, and a wiring that connects the drain of the nanopore FET to the peripheral circuits and a wiring that connects the source of the selection transistor to the peripheral circuits are formed by patterning.

Figure 26:
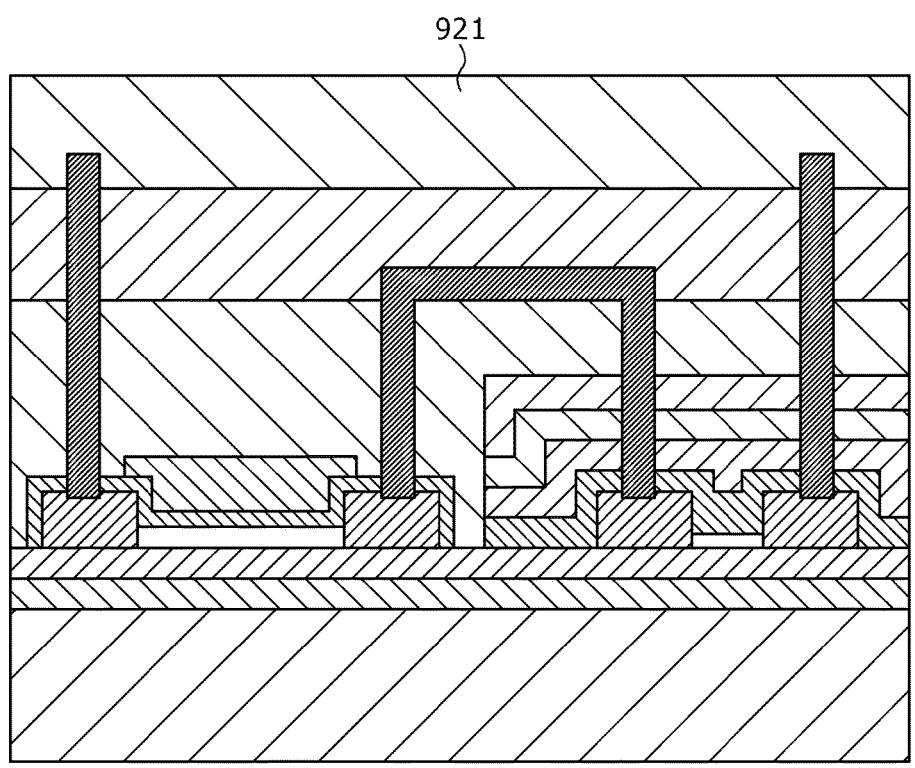
FIG. 26 is a diagram for explaining a process of the manufacturing method of the semiconductor device of the first embodiment.

(13) As shown in FIG. 26, a silicon nitride film 921 is deposited as an interlayer film, and the deposited silicon nitride film 921 is flattened by the CMP method.

Figure 27:
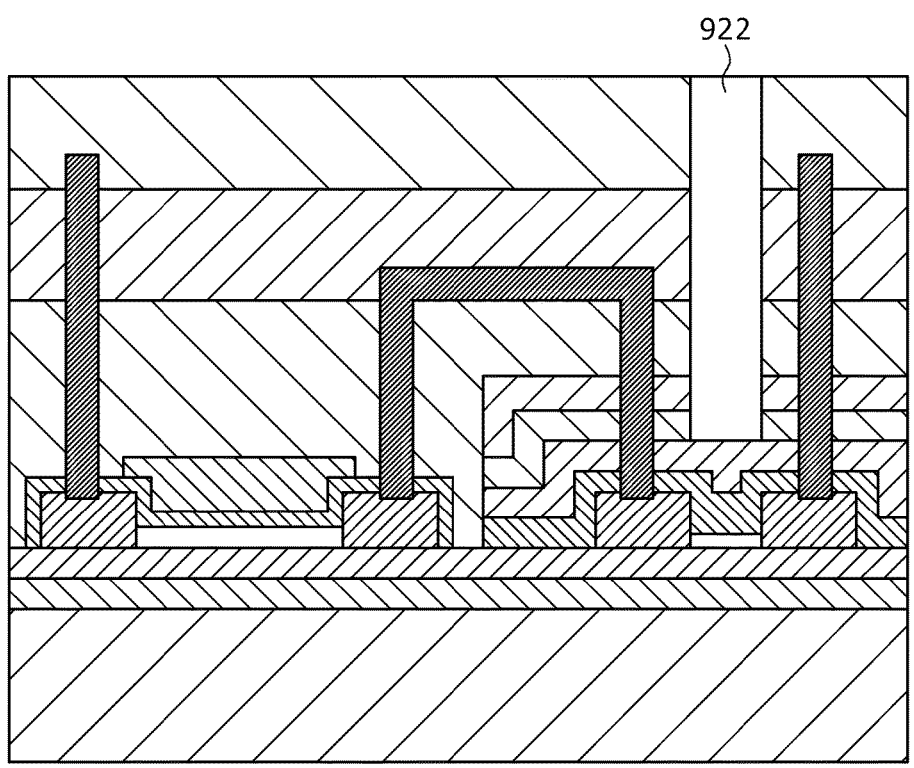
FIG. 27 is a diagram for explaining a process of the manufacturing method of the semiconductor device of the first embodiment.

(14) As shown in FIG. 27, parts of the insulating films over the vicinity of a place in which a nanopore is to be formed are etched away 922; the silicon substrate at the back side is etched away using a KOH aqueous solution; and finally a nanopore is formed in the vicinity of the channel by etching.

With the use of the above-described manufacturing method, a vertical gate transistor, which has a thermally-oxidized film as its gate oxidized film, with high reliability, a low variation, and a good off characteristic, can be prepared as a selection transistor for a nanopore FET.

Second Embodiment

Figure 13:
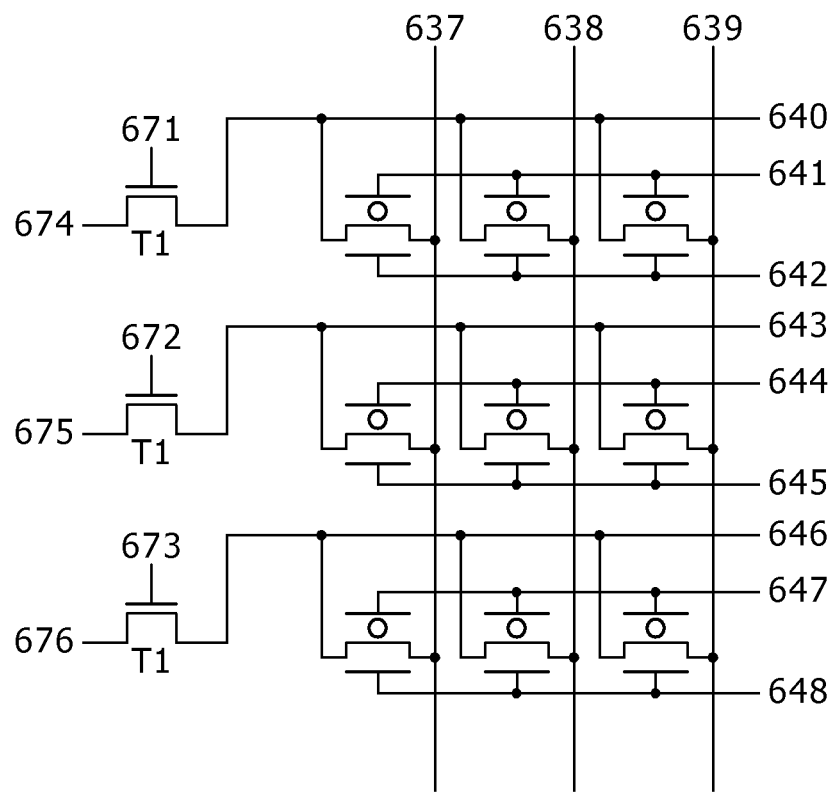
FIG. 13 is a diagram for explaining a circuit in which a selection transistor is prepared for each row according to a second embodiment.

As shown in FIG. 13, it is also possible to prepare a selection transistor for each row according. For example, in the case of selecting the uppermost row, potential differences are set between a read line 674 and a wiring 637, between the read line 674 and a wiring 638, and between the read line 674 and a wiring 639 respectively. In this case, it will be assumed that the potential of the read line 674>the potential of the wiring 637; the potential of the read line 674>the potential of the wiring 638; and the potential of the read line 674>the potential of the wiring 639. Furthermore, a voltage applied to a wiring 671 is set higher than a voltage applied to the read line 674. In addition, two different gate voltages are applied to a wiring 641 and to a wiring 642 respectively so that channel currents optimal for detections by nanopore FETs flow. With such a setting as above, detection currents flow out from the sensors in the uppermost row, and they flow into the peripheral circuit parts via read lines 637, 638, and 639. In such a way, the sensors in the uppermost row can be selected.

On the other hand, a voltage of a wiring 672 is set smaller than a voltage of a wiring 643 and the voltage of the wiring 672 is set smaller than a voltage of a read line 675, or a voltage of a wiring 673 is set smaller than a voltage of a wiring 646 and the voltage of the wiring 673 is set smaller than a voltage of a read line 676 so that any of the channel currents of nanopore FETs in the middle row and in the lowermost row do not flow. In such a way, the sensors in the middle row and the lowermost row can be deselected. A row to be selected is changed from the uppermost row to the middle row and to the lowermost row sequentially, and by setting two rows other than the selected row deselective, signals from sensors in each row can be obtained one row-by-one row. With the use of this method, it is sufficient to install one selection transistor for each row, and therefore, in the case of sensors being integrated into an LSI circuit, this method contributes to the reduction of the area of the LSI circuit. It goes without saying that the configuration that has been described in this embodiment can be applied to a generalized N-by-N sensor array.

Third Embodiment

Noises mixing with detection signals are not only noises due to leakage currents flowing out from deselected sensors, which have been described in the above embodiments, but also noises which are generated due to the influence from ambient surroundings and mix with the detection signals while the detection currents flow into peripheral signal processing circuits via read lines. A nanopore FET sensor is used for measurement in such a way that the outside of an insulating film located in the upper part of the nanopore FET sensor and the outside of an insulating film located in the lower part are filled with water solution including DNA. Therefore, the nanopore FET sensor is different from an ordinary device module that is used for measurement in the atmosphere, and the ion density in the solution around the read line of the nanopore FET sensor is not homogeneous. As a result, there is a high possibility that noises mix with the detection current of the nanopore FET sensor that flows through the read line.

In order to solve the above problem, it is effective to amplify the signal of the nanopore FET sensor before the signal is sent out to the read line. By amplifying the signal, it becomes possible to make the amount of the detection current and the differences among detection currents based on four kinds of base larger than the values of noises that are induced on the read line, and therefore the values of the noises induced on the read line due to the influence from ambient surroundings can be relatively smaller than the detection current or the differences among the detection currents (the S/N ratio can be made larger). As a result, the accuracy of the measurement is improved.

Figure 10:
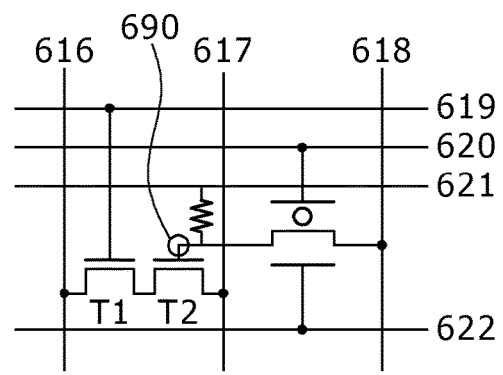
FIG. 10 is a diagram for explaining the circuit to which an amplifier transistor and a selection transistor shown in a third embodiment are added.

FIG. 10 is a diagram showing a configuration in which an amplifier mechanism is installed between a read line and a nanopore FET. Reference numeral T2 denotes an amplifier transistor, and reference numeral T1 denotes a selection transistor. The gate of the amplifier transistor T2 is connected to the source of the nanopore FET and a wiring 621. The wiring 621 is connected to a constant voltage source (for example, the ground), and there is a resistor between the constant voltage source and the gate of the amplifier transistor T2. It is desirable that the value of this resistor should be about the same as the value of the channel resistor of the nanopore FET when detection is performed using the nanopore FET.

In the case where the signal of the FET sensor is read out, the potential difference is set between the potentials of a read line 616 and a wiring 617. For example, it will be assumed that the potential of the wiring 617<the potential of the read line 616. Furthermore, the voltage of a wiring 619 is set higher than the voltage of the read line 616 and the voltage of the wiring 617. With the above setting, the selection transistor T1 is turned on. In addition, the potential difference is set between the potentials of the wiring 621 and a wiring 618. For example, it will be assumed that the potential of the wiring 621>the potential of the wiring 618. Furthermore, two different gate voltages are applied to a wiring 620 and to a wiring 622 respectively so that a channel current optimal for the detection by the nanopore FET flows.

Figure 5:
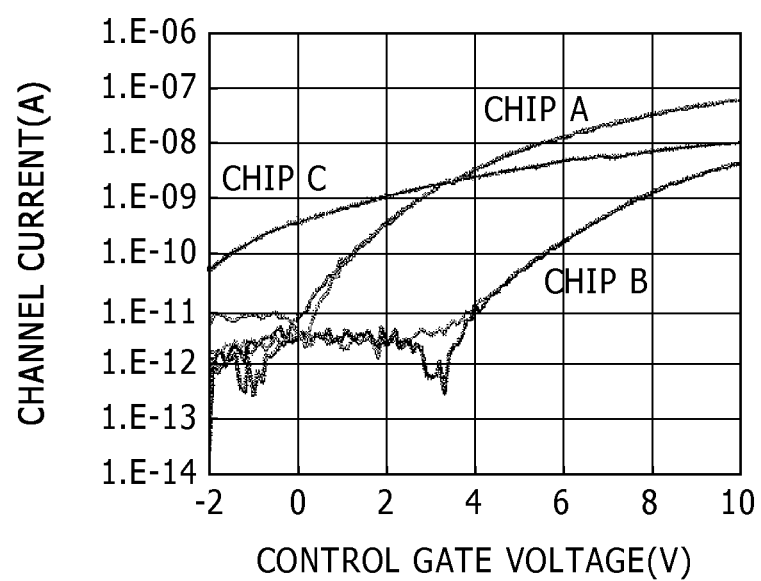
FIG. 5 is a diagram showing experimental results showing the control gate voltage dependence characteristics of the channel currents of NMOS type nanopore FET sensors.
Figures 6A, 6B:
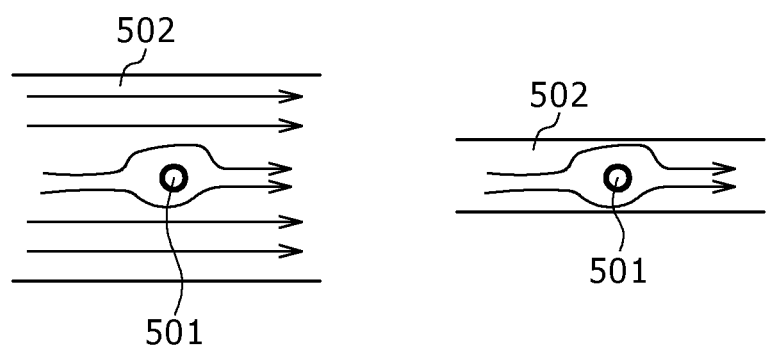
FIG. 6A and FIG. 6B are diagrams for explaining a reason for the variation of the threshold of a nanopore FET sensor to become very large depending on the amount and location of a fixed charge if the fixed charge exists in an insulating film near to the side face of a channel or on the surface of the interface between the insulating film and the channel.

In the case where the voltages of the wirings 620, 622, 617, 618, and 621 are constant and the value of the resistor connected to the wiring 621 is constant, the value of the channel resistance of the nanopore FET varies in accordance with types of object to be examined or four kinds of base, and therefore the ratio of the value of the channel resistance to the value of the resistor connected to the wiring 621 varies accordingly. As a result, the potential of an encircled portion 690 varies in accordance with the types of object to be examined or the four kinds of base. The value of a signal detected by the nanopore FET during DNA detection is 100 nA at the highest estimating from the experiment results described in the first embodiment (refer to FIG. 5). In addition, the differences among the currents based on four types of base are lower than this value.

Figure 12A:
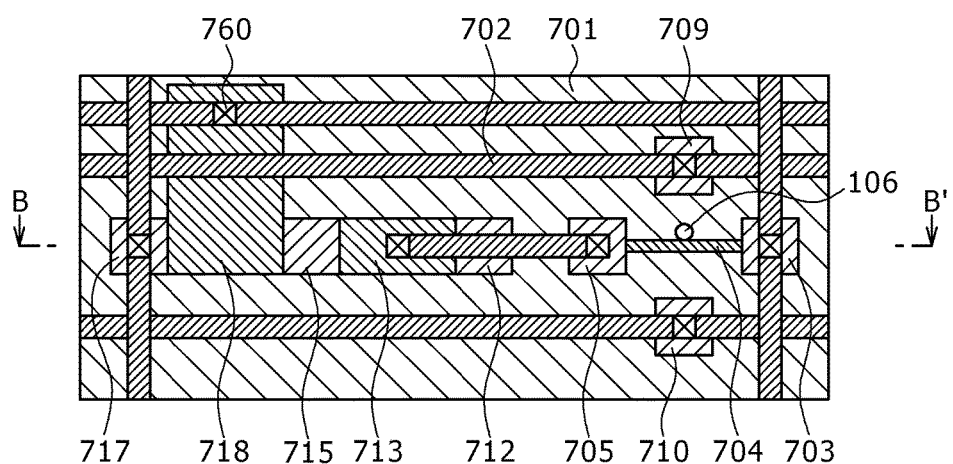
FIG. 12A shows the top view of a set of a nanopore FET, a selection transistor, and an amplifier transistor of the third embodiment.
Figure 12B:
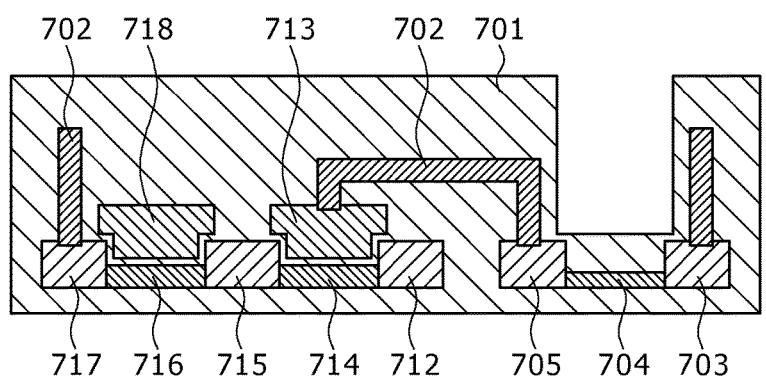
FIG. 12B shows a cross-sectional view taken along the line B-B' of FIG. 12A.

In the case where the nanopore FET is driven with the stable value of a detection current about 10 nA, if the value of a current flowing the amplifier transistor T2 is set more than 10 nA, this value can be made larger than the value of the detection current directly emitted from the nanopore FET and the difference among detection currents based on four kinds of base, and therefore the S/N ratio can be larger. The smaller the S value (the subthreshold coefficient) of the amplifier transistor is, the larger the transistor current difference due to the gate voltage difference can be. In other words, the potential difference at the portion 690 generated by four kinds of base can be converted into a larger current difference. The thickness of an insulating film between the channel and the gate of a vertical gate transistor can be set less than 3 nm, that is to say, very thinner in comparison with that of a side gate transistor due to the difference between manufacturing methods of both transistors. Therefore, as shown in FIG. 12A and FIG. 12B, it is desirable that an amplifier transistor should also be formed using a vertical gate configuration.

Figure 11:
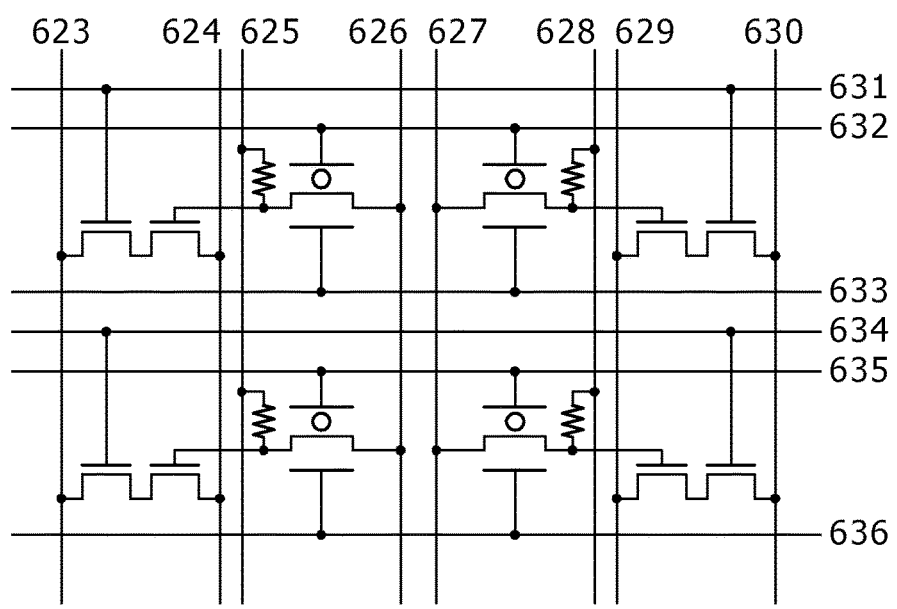
FIG. 11 is a diagram for explaining an example of arraying the circuit shown in FIG. 10 of the third embodiment.

FIG. 11 is a diagram showing an example of a 2-by-2 array including four circuits each of which is equivalent to the circuit shown in FIG. 10. It goes without saying that this 2-by-2 array can be expanded into a generic N-by-N array.

For example, in the case of selecting an upper row, voltages are applied to this 2-by-2 array so that the voltage of a wiring 631>the voltage of a read line 623>the voltage of a wiring 624, and the voltage of the wiring 631>the voltage of a read line 630>the voltage of a wiring 629. Furthermore, the voltage relation between a wiring 632 and a wiring 633 and the voltage relation between a wiring 625 and a wiring 626, and the voltage relation between the wiring 632 and the wiring 633 and the voltage relation between a wiring 627 and a wiring 628 are adjusted so that currents flow through nanopore FETs in the upper row. With such a setting, the gate potentials of amplifier transistors in the upper row vary depending on individual objects to be examined, and these variations of the gate potentials are amplified by the channel currents of the amplifier transistors respectively, and the amplified variations are sent out to read lines 623 and 630 respectively.

On the other hand, in a lower row that is not selected, the voltage of the gate 634 of selection transistor is set lower than the voltages of the read lines 623 and 630 and the voltages of the wirings 625 and 628 so that the signals do not flow from nanopore FETs to the read lines.

FIG. 12A shows the top view of a set of a nanopore FET, a selection transistor, and an amplifier transistor, and FIG. 12B shows a cross-sectional view taken along the line B-B' of FIG. 12A. In FIG. 12A, for easy understanding, insulating films located over the channel of the nanopore FET are omitted. In FIG. 12A and FIG. 12B, reference numeral 701 denotes an insulating film; 702 denotes a wiring; 703 denotes the drain of the nanopore FET; 704 denotes the channel of the nanopore FET; 705 denotes the source of the nanopore FET; 709 denotes the control gate of the nanopore FET; 710 denotes the back gate of the nanopore FET; 712 denotes the drain of the amplifier transistor; 713 denotes the gate of the amplifier transistor; 715 denotes the source of the amplifier transistor and the drain of a selection transistor; 717 denotes the source of the selection transistor; 718 denotes the gate of the selection transistor; 106 denotes a nanopore; and 760 denotes contact portions to gates, sources, and drains.

Wirings that run vertically or horizontally are connected to the peripheral signal processing circuits while making contacts with electrodes in accordance with, for example, the circuit diagram shown in FIG. 11. When the nanopore FET sensor 100 is active, there is a solution including an object to be examined over the upper part and under the lower part of the insulating film 701 of the nanopore FET sensor FET 100, and when DNA passes through the nanopore of the nanopore FET sensor 100, the value of the channel current varies in accordance with the signal differences among four kinds of base, and the four kinds of base can be identified respectively by reading the variation of the channel current.

Fourth Embodiment

Figure 28A:
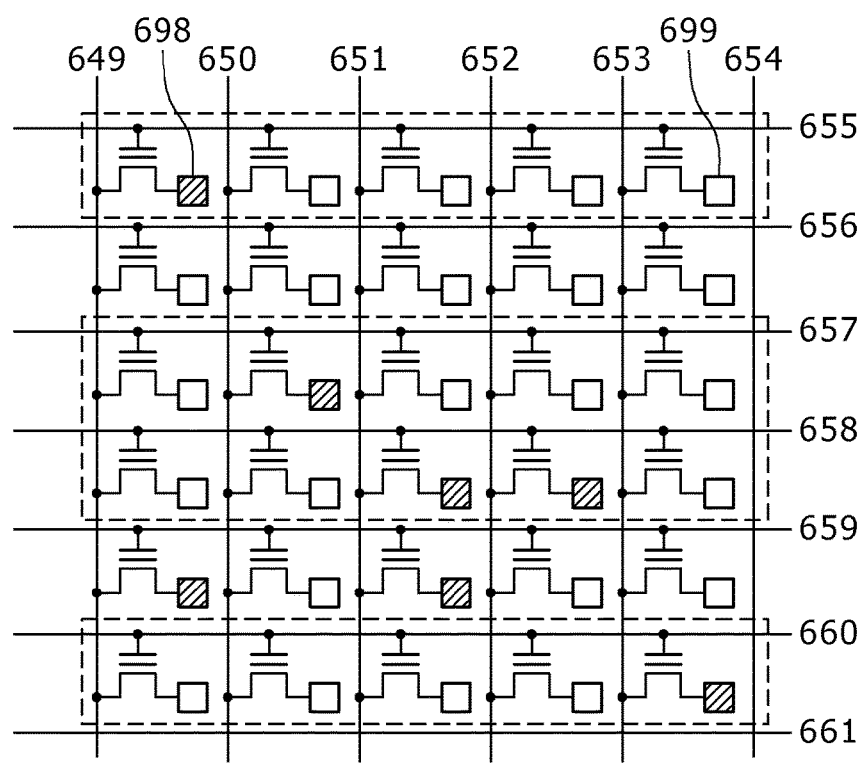
FIG. 28A is a diagram for explaining a circuit having a configuration in a selection transistor having a charge storage layer and a sensor to be selected as described in a fourth embodiment are parallelized.
Figure 28B:
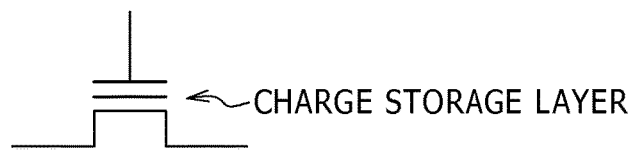
FIG. 28B is a diagram showing a cell of a selection transistor having a charge storage layer.

FIG. 28A shows a diagram in a selection transistor and a sensor to be selected are parallelized. In FIG. 28A, reference numerals 698 and 699 denote sensors respectively. A patterned sensor such as a sensor denoted by reference numeral 698 is a sensor that outputs a signal about an object to be examined normally. On the other hand, an outlined sensor such as a sensor denoted by reference numeral 699 is a sensor that does not output a signal about an object to be examined normally. In the case where good sensors and bad sensors mixedly exist as shown in FIG. 28A, if detection is performed by sequentially sending the signals of sensors for each row to read lines, because the signals of bad sensors are also detected together with the signals of good sensors, the total detection time is wastefully increased by the time needed for the detection of the bad sensors. Therefore, as shown in FIG. 28A, it is advantageous to select one or fewer good sensor to measure in one row and detect good sensors selected in all the rows in a lump.

To put it concretely using FIG. 28A, if four rows surrounded with dashed lines are selected, each of five columns includes only one good sensor to be examined. When those four rows are selected at the same time, signals from five good sensors are output to the read lines 649 to 653. On the other hand, because signals from bad sensors work as noises, they have to be cut. It is preferable that, in order to cut the signals from the bad sensors, a fuse should be installed between each sensor and the relevant read line, and a fuse between each bad sensor and the relevant read line is set off so that a current does not flow.

As an example of an element to play the role of the fuse, there is a kind of selection transistor that has a charge storage layer between its gate and channel and works as a memory transistor. If this selection transistor attached to a bad sensor is an NMOS transistor, electrons are charged, which effectively prevents a current from flowing between the sensor and the read line even if a voltage is applied to this selection transistor. After whether each sensor is good or bad is measured and memorized in advance by accessing each sensor and checking whether a current suitable for detection flows out from each sensor or not, charges are stored in the charge storage layers of selection transistors attached to bad sensors by applying voltages to the read lines 649 to 653 and to gates 655 to 660. One of methods for injecting charges is a method in which, by using voltage differences between the gate wirings and the read lines, tunnel currents are flowed from the channels to the insulating films, and the charges are stored.

The abovementioned operation makes it possible to read several rows in a lump in comparison with the case where signals are selectively and sequentially read one row-by-one row, which leads to the reduction in the total detection time and to the improvement of throughput. In addition, in the case where the time period of the signal variation of a sensor influenced by an object to be examined is short, if the signals of sensors for each row are sequentially read, there is a possibility that, during the time period while sensors for a certain row are set deselective, the signal variation of any of the sensors for the certain row is missed. On the other hand, because several rows can be examined in a lump in this embodiment, the abovementioned possibility can be reduced.

It will be apparent from the above description that the sensor described in this embodiment can be applied not only to a nanopore FET, but also to a general sensor.

Figure 29:
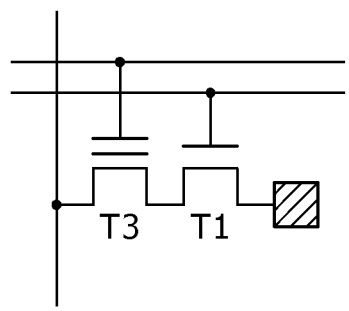
FIG. 29 is a diagram for explaining a circuit having the configuration of a series circuit including a selection transistor and a memory transistor instead of a selection transistor having a charge storage layer according to the fourth embodiment.

Furthermore, although the example in which a selection transistor has a memory function has been described in this embodiment, it is conceivable that a selection transistor and a memory transistor are independently installed. To put it concretely, as shown in FIG. 29, a selection transistor T1 and a memory transistor T3 can be connected in series between a read line and a sensor (it is also all right if the connection order of the selection transistor T1 and the memory transistor T3 is reversed).

Fifth Embodiment

Figure 30:
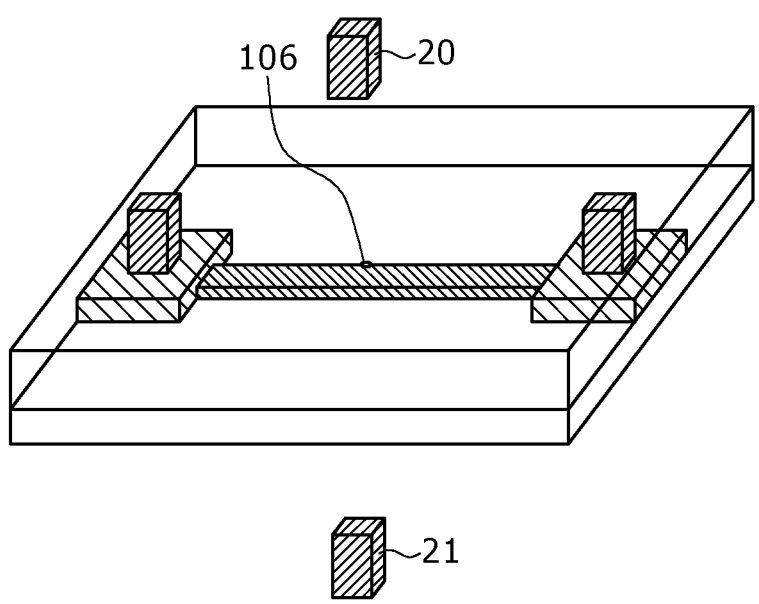
FIG. 30 is a schematic view for explaining the configuration of a nanopore FET sensor having no gate according to a fifth embodiment.

A configuration including a selection transistor or a configuration including a combination of a selection transistor and a gain cell can be effectively used for the configuration of a nanopore FET sensor with no gate (refer to FIG. 30). FIG. 30 is a diagram showing the configuration of a nanopore FET sensor with no gate, and reference numerals 20 and 21 are gate electrodes to drive the FET disposed in a solution. A detection method performed using the nanopore FET with no gate is a method in which the variation of the channel current of the nanopore FET sensor with no gate, which occurs when DNA passes through the nanopore of the nanopore FET sensor, is detected, and therefore it is the same as the detection method performed by a nanopore FET sensor with gates in that regard. Unlike the case of the nanopore FET with gates, a current does not flow concentratedly on the pore side in the channel, and therefore the nanopore FET sensor with gates is more sensitive. On the other hand, because the channel of the nanopore FET with no gate is made of a thin film, a large variation of the threshold of the nanopore FET with no gate is a problem although the variation is not so large than the variation of the threshold of the nanopore FET with gates.

Figure 31:
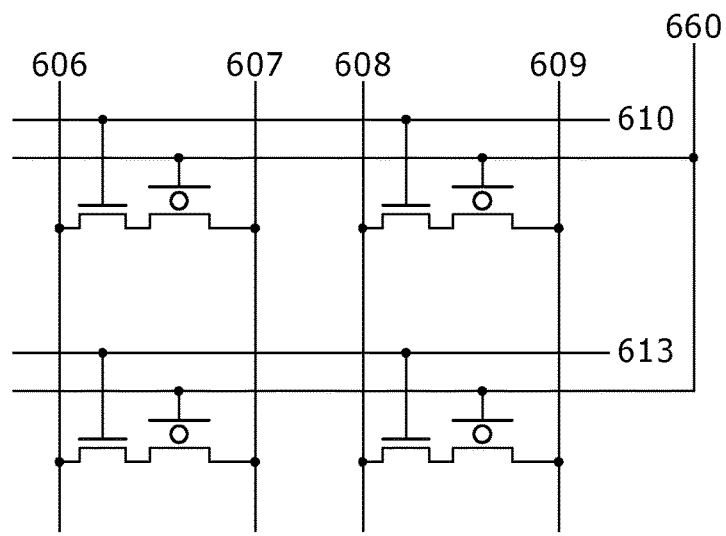
FIG. 31 is a diagram for explaining an example of a circuit of the fifth embodiment.

In order to solve the above problem, it is effective to install a selection transistor for each sensor as shown in the above-described embodiments. FIG. 31 is a diagram showing a circuit of a fifth embodiment. Reference numerals 606 and 608 denote read lines, 660 denotes a wiring connected to gate electrodes in a solution (corresponding to the gate electrodes denoted by 20 and 21 in FIG. 30), 610 and 613 denote wirings connected to the gate electrodes of selection transistors, and 607 and 609 denote wirings connected to the drain electrodes of sensors. Because the behavior scheme of the circuit shown in FIG. 31 is the same as described in the previous embodiments, the description of the behavior of the circuit is not repeated.

Figure 32:
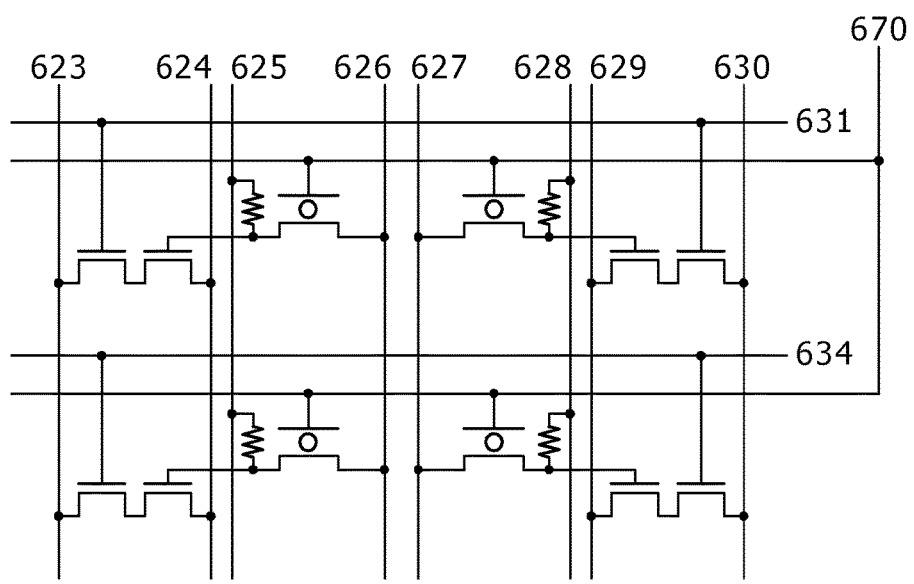
FIG. 32 is a diagram for explaining an example of a circuit including a sensor which is connected to a selection transistor and an amplifier transistor as described in the fifth embodiment.

In addition, it is also useful to attach an amplifier transistor to a sensor for the same reason as described in the third embodiment. FIG. 32 shows a circuit diagram in which a selection transistor and an amplifier transistor are attached to each sensor. Reference numeral 670 denotes a wiring connected to gate electrodes in a solution (the gate electrodes denoted by reference numeral 670 correspond to the gate electrodes denoted by reference numerals 20 and 21 in FIG. 30), 631 and 634 denote wirings connected to the gate electrodes of selection transistors, 630 and 623 denote read lines, and 624 and 629 denotes wirings connected to the drains of amplifier transistors. Because the behavior scheme of the circuit shown in FIG. 32 is the same as described in the previous embodiments, the description of the behavior of the circuit is not repeated.

It is preferable that the selection transistor and the amplifier transistor should be vertical gate transistors because of the reason described in the previous embodiments.

Sixth Embodiment

Figure 33:
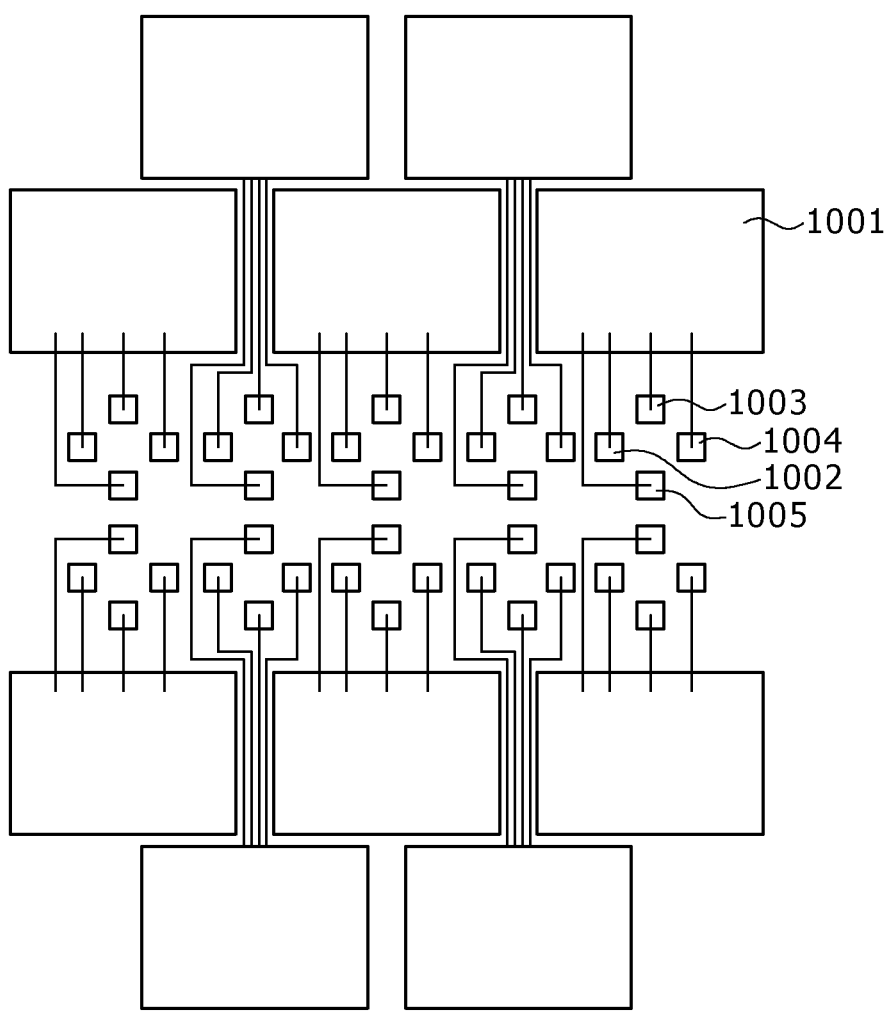
FIG. 33 is a diagram for explaining an example of a sensor array configured to read out all the sensors at the same time by preparing a peripheral signal processing circuit for a sensor of a sixth embodiment on a one-to-one basis.

The descriptions have been made so far with a prerequisite that sensors are arrayed by connecting some of the electrodes of sensors with shared wirings if they can be electrically connected to one another. In a sixth embodiment, a sensor array is configured in such a way that, without connecting the electrodes of sensors with shared wirings, each electrode of each sensor has its own wiring through which a signal is sent to the relevant peripheral circuit (in other words, without sequentially selecting or deselecting sensors one-by-one, signals from all the sensors can be read at the same time), and the top layout of the sensor array is shown in FIG. 33. The fact that the signals from all the sensors are read at the same time leads to the reduction in the total detection time and to the improvement of throughput. Furthermore, in the case where the time period of the signal variation of a sensor influenced by an object to be examined is short, if the signals of sensors for each row are sequentially read, there is a possibility that, during the time period while sensors for a certain row are set deselective, the signal variation of any of the sensors for the certain row is missed. On the other hand, because several rows can be examined in a lump in this embodiment, the abovementioned possibility can be reduced.

Reference numeral 1001 shown in FIG. 33 denotes a portion of a peripheral signal processing circuit for one sensor. Reference numerals 1002, 1003, 1004, and 1005 denote the source, gate, drain, and back gate of a nanopore FET respectively. The area of the portion of the peripheral signal processing circuit is larger than the area of the one sensor. As a result, the area of the peripheral signal processing circuit is dominant in the sum of the areas of the sensors and the area of the peripheral signal processing circuit. Therefore, it becomes possible to reduce the area of a sensor module by disposing the peripheral signal processing circuit in a twisted state as shown in the figure.

Although, in all the above-described embodiments, explanations have been made with a prerequisite that nanopore FET sensors are comprised of NMOS type FETs, the nanopore FET sensors can also be comprised of PMOS type FETs on the basis of principles similar to those described above.

REFERENCE SIGNS LIST 20,21 . . . gate electrodes in a solution
100 . . . nanopore FET sensors
101 . . . channel
102 . . . control gate
103 . . . source
104 . . . drain
105 . . . back gate
106 . . . pore
107 . . . wiring used for a contact
108 . . . insulating film
110 . . . nanopore FET
200 . . . DNA
501 . . . fixed charge
502 . . . side wall portion of the channel
601,606,608,616, 623,630,649,650,651,652,653,654,674, 675,676 . . . read line
602, 607, 609, 626, 627, 637, 638, 639 . . . Wiring connected to the drain of the nanopore FET
640,643,646 . . . Wiring connected to the source of the nanopore FET
603,610,613,619,631,634,655,656,657,658,659,660,661, 671,672,673 . . . Wiring connected to the gate of the selection transistor
604,611,614,620,632,635,641,644,647 . . . Wiring connected to the control gate of the nanopore FET
605,612,615,622,633,636,642,645,648 . . . Wiring connected to the back gate of the nanopore FET
617,624,629 . . . wiring connected to the drains of amplifier transistor
621,625,628 . . . wiring connected to the gate of amplifier transistor
660,670 . . . gate electrodes in a solution
701 . . . insulating film
702 . . . wiring
703 . . . the drain of the nanopore FET
704 . . . the channel of the nanopore FET
705 . . . the source of the nanopore FET
706 . . . the drain of the selection transistor
707 . . . the source of the selection transistor
708 . . . the channel of the selection transistor
709 . . . the control gate of the nanopore FET
710 . . . the back gate of the nanopore FET
712 . . . the drain of the amplifier transistor
713 . . . the gate of the amplifier transistor
714 . . . the channel of the amplifier transistor
715 . . . the source of the amplifier transistor
716 . . . the channel of the selection transistor 717 . . . the source of the selection transistor
718 . . . the gate of the selection transistor
750 . . . the gate of the selection transistor
760 . . . contact portions to gates, sources, and drains
901 . . . silicon substrate
902,921 . . . silicon nitride film
903 . . . silicon dioxide film
904 . . . the drain region
905 . . . the channel of the nanopore FET
906,908,912 . . . silicon dioxide film
907,909,914,920,921 . . . silicon nitride film
911 . . . nondoped polysilicon
913 . . . the gate electrode of the selection transistor
915,916,917,918,919 . . . wiring
922 . . . the pore of the insulating films over the vicinity of a place in which a nanopore is to be formed are etched away
1001 . . . peripheral signal processing circuit
1002 . . . the source of a nanopore FET
1003 . . . the gate of a nanopore FET
1004 . . . the drain of a nanopore FET
1005 . . . the back gate of a nanopore FET

What is claimed is:

1. A semiconductor device, comprising:
 a source, a drain, and a channel connecting the source and the drain formed on an insulating film;
 a control gate is, or a control gate and a back gate are, formed fronting onto one side face of the channel or formed fronting onto both side faces of the channel via the insulating film;
 a plurality of sensors each having a nano-sized pore through which an object to be examined passes and formed near to the side face of the channel fronting onto the control gate through the insulating films; and
 a plurality of selection transistors each capable of electrically selecting or deselecting a detection signal output of a relevant one of said sensors;
 wherein each of the selection transistors is configured as a memory transistor with a charge storage layer formed between its gate and channel,
 wherein a plurality of combinations comprised of one of the sensors and one of the selection transistors are disposed in an array configuration,
 wherein selection transistors connected to defective sensors are set to a deselective state by a peripheral circuit using a representative storing charge which is one of at least two storing charges, in the memory transistor charge storage layers of the selection transistors through voltage application by the peripheral circuit, said deselective state being based on a previous determination by the peripheral circuit of a sensor being a defective sensor, said previous determination obtained by operating each said sensor in an advance to determine, by the peripheral circuit, whether a current suitable to detection is output by said sensor, and
 wherein a group of said sensors in several rows of the array are set readable in a group by the peripheral circuit under a condition such that outputs of a plurality of non-defective sensors do not overlap in each column of the array.

2. The semiconductor device according to claim 1, further comprising:
 amplifier transistors, a gate of each of the amplifier transistors being connected to the source of one of the sensors outputting a channel current and to a constant voltage source via a resistor,
 wherein a plurality of combination circuits, each of which includes one amplifier transistor and one selection transistor that are connected to each other and further includes one sensor connected thereto, are disposed in an array configuration.

3. The semiconductor device according to claim 1, being configured in such a way that each of the selection transistors having charge storage layers respectively is replaced by a series configuration of a selection transistor having no charge storage layer and a memory transistor.

4. The semiconductor device according to claim 1, wherein the selection transistors are vertical gate transistors.

5. The semiconductor device according to claim 2, wherein the amplifier transistors are vertical gate transistors.

6. The semiconductor device according to claim 2, wherein the selection transistors are vertical gate transistors.

7. The semiconductor device according to claim 3, wherein the selection transistors are vertical gate transistors.

* * * * *